(12) United States Patent
Watanabe

(10) Patent No.: US 7,677,726 B2
(45) Date of Patent: Mar. 16, 2010

(54) MANUFACTURING METHOD FOR SPECTACLE LENS AND SPECTACLE LENS

(75) Inventor: Takatsugu Watanabe, Tokyo (JP)

(73) Assignee: Hoya Corporation, Tokyo (JP)

( * ) Notice: Subject to any disclaimer, the term of this patent is extended or adjusted under 35 U.S.C. 154(b) by 413 days.

(21) Appl. No.: 11/630,325

(22) PCT Filed: Jun. 27, 2005

(86) PCT No.: PCT/JP2005/011709

§ 371 (c)(1),
(2), (4) Date: Jan. 31, 2007

(87) PCT Pub. No.: WO2006/001409

PCT Pub. Date: Jan. 5, 2006

(65) Prior Publication Data

US 2008/0273170 A1    Nov. 6, 2008

(30) Foreign Application Priority Data

Jun. 29, 2004  (JP) .............................. 2004-192063

(51) Int. Cl.
G02C 7/02 (2006.01)
(52) U.S. Cl. .................. 351/177; 351/159; 351/168
(58) Field of Classification Search .................. 351/177
See application file for complete search history.

(56) References Cited

U.S. PATENT DOCUMENTS

| | | | | |
|---|---|---|---|---|
| 5,056,909 A | * | 10/1991 | Brown et al. | 351/177 |
| 5,296,881 A | * | 3/1994 | Freeman | 351/177 |
| 5,898,473 A | * | 4/1999 | Seidner et al. | 351/161 |
| 6,637,880 B1 | | 10/2003 | Yamakaji et al. | |
| 7,080,906 B2 | * | 7/2006 | Lindacher | 351/161 |
| 2001/0031607 A1 | | 10/2001 | Shirayanagi | |
| 2002/0176052 A1 | | 11/2002 | Ueno | |
| 2004/0032565 A1 | | 2/2004 | Yamakaji et al. | |
| 2004/0174499 A1 | | 9/2004 | Toshima et al. | |
| 2005/0004694 A1 | | 1/2005 | Ueno | |
| 2005/0073648 A1 | | 4/2005 | Toshima et al. | |

FOREIGN PATENT DOCUMENTS

| | | |
|---|---|---|
| JP | A 2002-122824 | 4/2002 |
| JP | A 2002-202482 | 7/2002 |
| WO | WO 00/48035 | 8/2000 |
| WO | WO 02/35280 A1 | 5/2002 |
| WO | WO 03/000123 A1 | 1/2003 |
| WO | WO 03/057038 A1 | 7/2003 |

* cited by examiner

Primary Examiner—Jessica T Stultz
(74) Attorney, Agent, or Firm—Oliff & Berridge PLC

(57) ABSTRACT

To ensure optical performance within a permissible range, making outward appearance excellent, and making binocular vision comfortable. In cases where a difference of prescription including dioptric power between the right and left eyes is equal to or more than prescribed, when curvature of a first refracting surface and a second refracting surface of the right and left spectacle lenses is designed, binocular vision balanced design such as selection of at least either of a first or second refracting surface out of the right and left spectacle lenses, or an intermediate curvature of the first and second surfaces of the right and left spectacle lenses according to a dominant eye ratio so that a difference between curvature of the first refracting surfaces of right and left spectacle lenses is within a prescribed range after the right and left spectacle lenses fulfill prescription conditions containing dioptric power respectively, and optical performance of the right and left spectacle lenses are within their permissible ranges respectively.

7 Claims, 22 Drawing Sheets

Fig.5

| | | |
|---|---|---|
| 51 { | INQUIRY | |
| | 10 | ORDER SHOP (077801) DELIVERY ADDRESS (077801) METHOD OF SHIPMENT ( ) |
| 52 { | 20 | ITEM D( ) SHAPE (4) HELP METS PROCESSING (3) NO DESIGNATION USAGE (0) OUTDOORS |
| 53 { | 31 | R LENS(HOYOLUX SUMMIT Pro 1.6) L LENS( ) |
| | 32 | : ( ) : ( ) |

PRESCRIPTION Sph   Cyl   Ax   Add   MACHINING 1  MACHINING 2  MACHINING 3  DOMINANT EYE DESIGNATION

| 54 { | 41 | R ( +5.00 )( )( )( 2.00 )( )( )( )( YES ) |
|---|---|---|
| | 42 | L ( +4.00 )( )( )( 2.00 )( )( )( )( ) |

MANUFACTURER ITEM NUMBER   SIZE   LENZ EDGE   TYPE

| 55 { | 51 | FRAME(NL059T )( 56-16 )( 0000 ) METAL |
|---|---|---|
| | 52 | : ( )( )( ) |

LAYOUT  PD  NPD  SEG  EP  ET  BEVEL MODE  POSITION  SHAPE AND SIZE

| 56 { | 61 | R ( 33.0 )( )( )( )( )( 4 )AUTO( 0.0mm )( 0 )SMALL |
|---|---|---|
| | 62 | L ( 33.0 )( )( )( )( )( 4 )AUTO( 0.0mm )( 0 )SMALL |
| | 70 | |
| | 80 | NOTE ( HELP ) CUSTOMER'S NAME MESSRS ( ) |

CORRECTION/CANCELLATION NUMBER ( )   (CORRECTION:NUMBER ①/CANCELLATION:NUMBER ②)

Fig.7

| | +5D (RIGHT) | +4D (LEFT) |
|---|---|---|
| FIRST REFRACTING SURFACE CURVE (D) | 6.97 | 6.06 |
| SECOND REFRACTING SURFACE CURVE (D) | 2.19 | 2.19 |
| CENTER THICKNESS (mm) | 7.0 | 5.9 |
| OUTER DIAMETER (mm) | 70 | 70 |

(REFRACTIVE INDEX OF LENS n = 1, 6 OBJECT POINT IS AT AN INFINITE DISTANCE)

|  | +5D(RIGHT) | +4D(LEFT) |
|---|---|---|
| FIRST REFRACTING SURFACE CURVE( D ) | 6.97 | 6.97 |
| SECOND REFRACTING SURFACE CURVE( D ) | 2.19 | 3.15 |
| CENTER THICKNESS(mm) | 7.0 | 6.0 |
| OUTER DIAMETER(mm) | 70 | 70 |

(REFRACTIVE INDEX OF LENS n = 1, 6 OBJECT POINT IS AT AN INFINITE DISTANCE)

|  | +5D(RIGHT) | +4D(LEFT) |
|---|---|---|
| FIRST REFRACTING SURFACE CURVE (D) | 6.06 | 6.06 |
| SECOND REFRACTING SURFACE CURVE (D) | 1.22 | 2.19 |
| CENTER THICKNESS (mm) | 7.0 | 5.9 |
| OUTER DIAMETER (mm) | 70 | 70 |

(REFRACTIVE INDEX OF LENS n = 1, 6 OBJECT POINT IS AT AN INFINITE DISTANCE)

Fig.13

| | +6D (RIGHT) | +4D (LEFT) |
|---|---|---|
| FIRST REFRACTING SURFACE CURVE (D) | 8.10 | 6.06 |
| SECOND REFRACTING SURFACE CURVE (D) | 2.45 | 2.19 |
| CENTER THICKNESS (mm) | 8.0 | 5.9 |
| OUTER DIAMETER (mm) | 70 | 70 |

(REFRACTIVE INDEX OF LENS n = 1, 6 OBJECT POINT IS AT AN INFINITE DISTANCE)

Fig.15

| | +6D (RIGHT) | +4D (LEFT) |
|---|---|---|
| FIRST REFRACTING SURFACE CURVE (D) | 8.10 | 8.10 |
| SECOND REFRACTING SURFACE CURVE (D) | 2.45 | 4.36 |
| CENTER THICKNESS (mm) | 8.0 | 6.0 |
| OUTER DIAMETER (mm) | 70 | 70 |

(REFRACTIVE INDEX OF LENS n = 1, 6 OBJECT POINT IS AT AN INFINITE DISTANCE)

Fig.17

|  | +6D (RIGHT) | +4D (LEFT) |
|---|---|---|
| FIRST REFRACTING SURFACE CURVE (D) | 6.06 | 6.06 |
| SECOND REFRACTING SURFACE CURVE (D) | 0.25 | 2.19 |
| CENTER THICKNESS (mm) | 8.0 | 5.9 |
| OUTER DIAMETER (mm) | 70 | 70 |
| (REFRACTIVE INDEX OF LENS n = 1.6 OBJECT POINT IS AT AN INFINITE DISTANCE) | | |

|  | +6D (RIGHT) | +4D (LEFT) |
|---|---|---|
| FIRST REFRACTING SURFACE CURVE ( D ) | 6.60 | 6.60 |
| SECOND REFRACTING SURFACE CURVE ( D ) | 0.83 | 2.77 |
| CENTER THICKNESS ( mm ) | 8.0 | 5.9 |
| OUTER DIAMETER ( mm ) | 70 | 70 |
| (REFRACTIVE INDEX OF LENS n = 1.6 OBJECT POINT IS AT AN INFINITE DISTANCE) | | |

MANUFACTURING METHOD FOR SPECTACLE LENS AND SPECTACLE LENS

TECHNICAL FIELD

The present invention relates to a manufacturing method of a spectacle lens and a spectacle lens capable of obtaining both of an outward appearance and an optical performance, and obtaining a comfortable binocular vision, even when a difference of prescriptions including dioptric power between right and left eyes exceeds beyond a prescribed range.

BACKGROUND ART

Upon prescribing spectacle lenses to correct visual acuity, if the right and left eyes have the same visual acuity, the prescription is made by using lenses having the same refractive powers (dioptric powers) for both eyes. The right and left spectacle lenses thus prescribed are the same in curvature for a first refracting surface (the surface on an object side in a spectacles-wearing state, namely, a forward refracting surface) and a second refracting surface (the surface on an eye side in a spectacles-wearing state, namely, a rearward refracting surface) with each other, and since optical performance such as astigmatism, curvature of field, distortion aberration and the like is also the same as a matter of course, no problem based on the difference between right and left lenses occurs. It should be noted that refracting power (dioptric power) of spectacle lens is in general approximately the sum of refracting power of the first and second refracting surfaces and expressed by a unit called dioptric power (hereinafter referred to as D). The refracting power (surface power) of the first and second refracting surfaces is defined by curvature $\rho$ of each surface (the unit is 1/m, and the radius of curvature R is $1/\rho$) and a refractive index n of lens material as follows.

$$\text{surface power} = (n-1) \times \rho = (n-1)/R \quad (1)$$

In this case, the refracting power of the first refracting surface of a spectacle lens is called especially a base curve.

However, when prescriptions containing dioptric powers differ between the right and left eyes, either curvature of the first refracting surface or that of the second refracting surface, or both differ between the right and left eyes. Here, according to Tscherning's ellipse which is found by Tscherning as a mathematical solution to eliminate astigmatism of a spectacle lens, an optimum base curve (refracting power of the first refracting surface) to eliminate astigmatism differs according to dioptric power of lens. Therefore, according to the Tscherning's ellipse, when the visual acuity differs between the right and left eyes, base curves of right and left lenses need to be different. When a lens is designed according to the Tscherning's ellipse, if the difference in visual acuity between the right and left eyes is large, the right and left base curves differ remarkably. Even according to a Percival form proposed by Percival relating to the curvature of field of a spectacle lens, the same result is obtained. When seen by a person other than the person wearing the spectacles from outside, the surface shapes of the right and left spectacle lenses appear remarkably unbalanced. Therefore, although optical performance is good, appearance is very poor. Moreover, since base curves differ according to refracting power (dioptric power), it is disadvantageous even from the point of view of production costs.

Accordingly, from the view points to reduce process cost, to improve outward appearance of lens, and the like, base curves are made common within a prescribed dioptric power range. Especially, in the case of progressive power lenses, design of reference progressive refracting surface, in which distribution of astigmatism and distribution of curvature of field from distance vision to near vision via intermediate vision for each base curve take optimum arrangement according to dioptric power in the prescription, is practiced, the aforementioned optical factors excluding prescribed dioptric power need to be laterally equal. Therefore, it is absolutely necessary to adjust the base curves of right and left spectacle lenses the same. In such a case, according to the Tscherning's ellipse, since the larger the curvature of base curve to vision acuity, the more the astigmatism is improved in a practical range as a spectacle lens, usually, either of right and left spectacle lenses having larger curvature in base curve is used to the other one. Accordingly, when the right and left lenses contain plus dioptric power, base curve on a stronger side of the plus dioptric power is used, and when the right and left lenses both contain minus dioptric power, base curve on a weaker side of minus dioptric power is used. However, in the lenses produced in this manner, deviations from the optimum base curves corresponding to each vision acuity for the right and left eyes differ right and left, which results in unbalanced optical performance. As a method to solve such a disadvantage, ensure the optical performance within a permissible range, and make the outward appearance favorable, known is a method to put a difference in curvature of the first refracting surface between right and left lenses within a prescribed range after ensuring prescribed items, optical performance, and the like (refer to Patent Document 1).

[Patent Document 1] Japanese Patent Application Laid-open No. 2002-202482

DISCLOSURE OF THE INVENTION

Problems to be Solved by the Invention

Although lenses manufactured by the afore-mentioned method are excellent because they ensure optical performance within a permissible range while also achieving good appearance, they have a disadvantage in that they sometimes fail to ensure binocular performance.

The present invention is achieved under the afore-mentioned circumstances, and is aimed at providing a method for manufacturing and supplying spectacle lenses which keep the outward appearance good while ensuring optical performance within a permissible range, and further make binocular vision comfortable.

Means for Solving the Problems

A first means as a means for solving the afore-mentioned problems is such that:

a method of manufacturing a spectacle lens for designing and manufacturing right and left spectacle lenses whereby a spectacle is constituted, having different prescriptions including dioptric power between right and left eyes, wherein when the difference of prescriptions including dioptric power is a prescribed value or more between the right and left eyes, the method comprises:

selecting curvatures of first and second refracting surfaces of at least one of the right and left spectacle lenses based on a dominant eye ratio, so that the difference in curvature of the first refracting surface between the right and left spectacle lenses is within a prescribed range, after respective right and left spectacle lenses are made to fulfill the prescription conditions including dioptric power and the optical performance of the right and left spectacle lenses are within a permissible range, assuming that refracting surfaces on the front side (object side) of right and left spectacle lenses are taken as a first refracting surface and the rear side thereof (eyeball side) are taken as a second refracting surface, when the curvature of the first and second refracting surfaces of right and left spectacle lenses is designed, wherein the dominant eye ratio is the ratio of the optical performance index of the spectacle lens for the dominant eye side to that of the spectacle lens for the non-dominant eye out of the right and left eyes, the optical performance index is exponentiation of the distinct vision field spatial extent in the optical performance of respective spectacle lenses for the right and left eyes, expressed by index of I (Di, Bi) when the first refracting surface is Bi (unit: dioptric power), and the dioptric power of the prescription is Di (unit: dioptric power), therefore the optical performance index of the spectacle lens for the dominant eye is expressed by I (Dmj, B1) where an optional first refracting surface of this lens is B1 and the dioptric power of the prescription is Dmj, while the optical performance index of the spectacle lens for the non-dominant eye is expressed by I (Dmn, B2) where an optional first refracting surface of this lens is B2 and the dioptric power of the prescription is Dmn, and therefore, the aforementioned dominant eye ratio is expressed by I (Dmj, B1):I (Dmn, B2) which is the ratio of the optical performance indexes of the left and right spectacle lenses.

A second means is, the method of manufacturing a spectacle lens according to the first means, wherein the difference in dioptric power between the right and left eyes is 0.5 dioptric power (unit of refracting power of a spectacle lens, referred to as D, hereinafter) or more when dioptric power in the prescriptions contains plus dioptric powers, while the difference in dioptric power between the right and left eyes is 1.0 D or more when the prescription of the aforementioned dioptric power contains minus dioptric powers, and at the same time, a difference in curvature between the first refracting surfaces of the right and left spectacle lenses is 1.0 D or less.

A third means is, the spectacle lens and the method of manufacturing a spectacle lens according to the first or the second means, wherein the optical performance is at least one out of astigmatism, curvature of field, distortion aberration and the like.

A fourth means is, the method of manufacturing a spectacle lens according to any means from the first to third means, wherein selection of the curvature of the first refracting surface of at least right or left spectacle lens is for making this curved surface an aspheric surface.

A fifth means is, the method of manufacturing a spectacle lens according to any one of claim 1 to claim 4, wherein the dominant ratio is defined in a range from 4:6 to 3:7 so as to give precedence to the optical performance index of the spectacle lens for the non-dominant eye over that of the spectacle lens for the dominant eye but the precedence is not protruded when dynamic recognition of depth in space is required, while on the contrary, the dominant eye ratio is defined in a range from 6:4 to 7:3 so as to give precedence to the optical performance index of the spectacle lens for the dominant eye over that of the spectacle lens for the non-dominant eye but the precedence is not protruded when static discrimination of an object in space is required.

A six means is, the method of manufacturing a spectacle lens according to the fifth means, wherein whether the dynamic recognition of depth in space is required or the static discrimination of an object in space is required is determined according to dominant eye information of individual spectacle lenses wearers, wherein the dominant eye information refers to the information of an individual spectacle lenses wearer and is a combination of a usage condition of the spectacle lenses whether a depth in space should be dynamically recognized when wearing the spectacle lenses outdoors, or whether an object in space should be statically discriminated when wearing the spectacle lenses indoors; a functional condition of the spectacle lenses whether the depth in space should be dynamically recognized in a range from a distance vision to a near vision as is the case of driving a car, or whether an object in space should be statically discriminated mainly only in the near vision as is the case of an OA work; and a physical condition of a spectacle wearer which one of the right and left eyes is selected to be a dominant eye when gazing at an object by using the distance vision, intermediate vision, and near vision, respectively.

A seventh means is, the method of manufacturing a spectacle lens according to any one of the first to sixth means, wherein at least one of the right and left spectacle lenses has a toric or atoric surface.

An eighth means is, a method of manufacturing a spectacle lens for designing and manufacturing right and left spectacle lenses whereby a spectacle is constituted, having different prescriptions including dioptric power between right and left eyes, wherein when the difference of prescriptions including dioptric power is a prescribed value or more between the right and left eyes, the method comprises:

selecting a curvature of an intermediate first refracting surface of the right and left spectacle lenses based on a dominant eye ratio, so that the difference in curvature of the first refracting surface between the right and left spectacle lenses is within a prescribed range, after respective right and left spectacle lenses are made to fulfill the prescription conditions including dioptric power and the optical performance of the right and left spectacle lenses are within a permissible range, assuming that refracting surfaces on the front side (object side) of right and left spectacle lenses are taken as a first refracting surface and the rear side thereof (eyeball side) are taken as a second refracting surface, when the curvature of the first and second refracting surfaces of right and left spectacle lenses is designed.

A ninth means is, the method of manufacturing a spectacle lens according to the eighth means, wherein the difference in dioptric power between the right and left eyes is 0.5 D or more when dioptric power in the prescriptions contains plus dioptric powers, while the difference in dioptric power between the right and left eyes is 1.0 D or more when the prescription of the aforementioned dioptric power contains minus dioptric powers, and at the same time, a difference in curvature between the first refracting surfaces of the right and left spectacle lenses is 1.0 D or less.

A tenth means is, a method of manufacturing a spectacle lens for manufacturing a spectacle lens by providing a customer side computer arranged on an orderer side of spectacle lenses and a manufacture side computer connected to the customer side computer enabling exchange of information, and performing computational processing with the customer side computer and the manufacture side computer according to prescribed input operation to execute necessary processing for order or order reception of spectacle lenses while mutually exchanging information, wherein when machining condition data necessary for machining of spectacle lenses such as spectacle lens information, spectacle frame information, prescription values, layout information, machining instruction information, dominant eye information (combination of usage condition, functional condition of spectacle lenses and physical condition of a wearer), or the like are transmitted from the customer side computer to the manufacture side computer, a spectacle lens design program mounted on the manufacture side computer comparatively studies factors containing optical performance of the right and left eyes from the lens designing data prepared in advance based on the data of the transmitted spectacle lens information, performs balance adjustment of factors containing optical performance of the right and left eyes according to the dominant eye information, and executes optical design of spectacle lenses to make dominant eye ratio suitable for the customer to determine right and left prescription lenses.

An eleventh means is, a method of manufacturing a spectacle lens for manufacturing a spectacle lens by providing a customer side computer arranged on an orderer side of spectacle lenses and a manufacture side computer connected to the customer side computer enabling exchange of information, and performing computational processing with the customer side computer and manufacture side computer according to prescribed input operation to execute necessary processing for order or order reception of spectacle lenses while mutually exchanging information, wherein when machining condition data necessary for machining of spectacle lenses such as spectacle lens information, spectacle frame information, prescription values, layout information, machining instruction information, dominant eye information (combination of usage condition, functional condition of spectacle lenses and physical condition of a wearer), or the like are transmitted from the customer side computer to the manufacture side computer, a spectacle lens design program mounted on the manufacture side computer, comprises selecting right and left lenses from a lens designing table prepared in advance, based on the data of the transmitted spectacle lens information;

comparing the difference in convex surface base curve between the selected right and left lenses;

performing balance adjustment of factors including optical performance of the right and left eyes according to the dominant eye information regarding the convex surface base curve, when the difference of the prescription including the dioptric power is equal to or more than prescribed and the difference in base curve is equal to or more than the reference previously established; and redesigning of the lenses to get a prescribed dominant eye ratio by approximating the convex surface base curve to the other base curve in aspheric shape.

A twelfth means is, the method of manufacturing a spectacle lens according to either of the ninth or tenth means, further comprising:

transmitting a display means for comparing data including a lens shape before adjusting the convex surface curves and a prescription value of the lens, with data including a lens shape after adjusting the convex surface curves and a prescription of the lens from the manufacture side computer disposed on the order reception side of the spectacle lenses to the customer side computer disposed on the orderer side of the spectacle lenses.

A thirteenth means is, a method of manufacturing a spectacle lens for manufacturing a spectacle lens by providing a customer side computer arranged on an orderer side of spectacle lenses and a manufacture side computer connected to the customer side computer enabling exchange of information, and performing computational processing with the customer side computer and manufacture side computer according to prescribed input operation to execute necessary processing for order or order reception of spectacle lenses while mutually exchanging information, wherein when machining condition data necessary for machining of spectacle lenses such as spectacle lens information, spectacle frame information, prescription values, layout information, machining instruction information, dominant eye information (combination of usage condition, functional condition of spectacle lenses and physical condition of a wearer), or the like are transmitted from the customer side computer to the manufacture side computer, a spectacle lens design program mounted on the manufacture side computer, comprises:

selecting right and left lenses from a lens designing table prepared in advance, based on the data of the transmitted spectacle lens information;

comparing the difference in convex surface base curve between the selected right and left lenses;

performing balance adjustment of factors including optical performance of the right and left eyes according to the dominant eye information regarding the convex surface base curve, when the difference of the prescription including the dioptric power is equal to or more than prescribed and the difference in base curve is equal to or more than the reference previously established; and redesigning of the lenses to get a prescribed dominant eye ratio by approximating the convex surface base curve to an intermediary base curve between convex surfaces of the right and left eyes in aspheric shape.

Effect of the Invention

According to the afore-mentioned first to third means, when the difference of the prescription including dioptric powers is equal to or more than prescribed (for instance, 1.0 D or more) between the right and left eyes, difference in prescriptional conditions including dioptric powers and in optical performance between right and left lenses is put within a permissible range, and a difference in curvature of the first refracting surface between right and left spectacle lenses is put within a prescribed range (for instance, 1.0 D or less), and by selecting curvatures of the first and second refracting surfaces of at least right or left spectacle lens according to the dominant eye ratio, it becomes possible to obtain spectacle lenses for spectacles, which ensures optical performance with a good outward appearance, and further ensures comfortable binocular vision.

The reason why such an effect like this can be obtained is considered as follows. Namely, it is known that one has a dominant eye (the eye mainly used when he looks something) similarly to that one has a dominant arm (the arm mainly used when he does something). According to a study made by the present inventor, the following fact has been found as for a dominant eye. For a case where stereoscopy with binocular vision is necessary, for instance, where a wide view or a sense of distance from front or from rear during driving is necessary, spectacle lenses design to apply weight on a spectacle lens on the dominant eye side is carried out in an attempt to make binocular vision comfortable. That is, optical performance such as astigmatism, curvature of field, distortion aberration and the like on the dominant eye side is made less (higher) than prescribed when compared with that of the lens on the non-dominant eye side. However, it is found unexpectedly that this causes degradation in ability of stereoscopy, which leads to shortage of sensibility to a sense of distance. The reason for this is found that when optical performance on the dominant eye side is made better than prescribed, it results in balance overemphasizing of the dominant eye, which leads to a state of obtaining a view as though with only one eye on the dominant eye side, causing unbalance in width of viewing fields between right and left directions due to narrowing of viewing field of the eye other than the dominant eye, and further, inviting shortage of sensibility to a sense of distance due to degradation of stereoscopic ability.

On the contrary, in cases of watching a play at a theater or working at an office with a computer where resolution for discriminating objects such as persons or letters is more important than a wide viewing field or a sense of distance, if spectacle lens design applying weight on a spectacle lens for the eye other than the dominant eye is carried out, it is found that it leads to watching of the object with an eye opposite to the dominant eye due to deterioration in visual acuity of the dominant eye, which causes ability deterioration in discrimination or recognition of persons or letters. From the result of such an elucidation, it is found that failure in balance adjustment of right and left spectacle lenses may lead to deterioration in binocular visual acuity or difficulty in binocular vision.

The present invention is based on the above elucidation result.

When considering a shape of the Tscherning's ellipse, which is mathematical solution to remove astigmatism in spectacle lenses, it is found that lenses having plus dioptric powers have a tendency to gradually increase in change of curvature of the base curve according to increase in lens dioptric power. On the contrary, lenses having minus dioptric powers have a tendency to gradually decrease in change of curvature of the base curve according to increase in lens dioptric power. This is because, shown by inclination of the Tscherning's ellipse, a lens having a plus dioptric power has a tendency to make its inclination gradually steeper while a lens having a minus dioptric power has a tendency to make its inclination gradually slower. As for a Percival form relating to curvature of field, it is in the same tendency.

Accordingly, when in a prescription including plus dioptric powers, a difference in dioptric power between right and left lenses is 0.5 D or more, the difference in curvature of the first refracting surfaces of spectacle lenses between the right and left eyes is within 1.0 D, while on the contrary, when in a prescription including minus dioptric powers, the difference in dioptric power between right and left lenses is 1.0 D or more, the difference in curvature of the first refracting surfaces of spectacle lenses between right and left lenses is preferably within 1.0 D.

As optical performance of a spectacle lens, astigmatism, curvature of field, distortion aberration, or the like can be cited, and since at least one of these factors is within a permissible range, it displays sufficient performance as a spectacle lens, and if both right and left spectacle lenses are within a permissible range, difference in performance between the right and left lenses can be seen as substantially equivalent, the performance as a pair of spectacles will be satisfactory.

Further, when indexes indicating optical performance of right and left binocular lenses are balanced according to dominant eye information, performance as spectacle lenses are further improved. For instance, when distribution of astigmatism is balanced, a state of imaging on the retina is balanced between the right and left eyes, which makes it easy to perform binocular vision. Since a curvature of field is a mean value of m (meridional) field and s (sagittal) field, when this distribution is balanced, an adjustment amount at the time of performing peripheral vision is also balanced, and binocular vision is easy to be performed. Since distortion aberration is strain of an image on the retina, when this is balanced, distortion of the image is balanced at the time of performing peripheral vision to facilitate performing of binocular vision. Though it is desirable to balance these aberration simultaneously, it is difficult to balance plural aberrations at the same time because there are only two refracting surfaces for forming a lens in a spectacle lens.

According to the afore-mentioned fourth to sixth means, by making at least the first refracting surface an aspheric surface, it becomes possible to realize not only lenses excellent in optical performance but also lenses having further better appearance by reducing difference in curvature of the first refracting surfaces between right and left lenses. Furthermore, by taking a dominant eye of each person wearing spectacle lenses as a design factor, it becomes possible to obtain spectacle lenses of comfortable binocular vision.

According to the afore-mentioned sixth means, by arranging at least a lens of spectacle lenses for right and left eyes to have a toric surface or atoric surface, it becomes possible to obtain spectacle lenses applicable to correct astigmatism. According to the afore-mentioned seventh to eighth means, since thus obtained lenses are excellent both in optical performance and appearance, and have a good balance between right and left lenses, it is possible to obtain spectacle lenses for spectacles having comfortable binocular vision. According to the afore-mentioned ninth to eleventh means, factors including optical performance such as astigmatism and a convex-surfaced base curve (first refracting surface) are compared and studied for right and left lenses, and adjusted in consideration of a balance of a dominant eye, Therefore, it is possible to supply spectacle lenses for excellent spectacles well balanced between right and left.

According to the afore-mentioned twelfth means, when the difference in prescription including dioptric powers between right and left eyes is more than prescribed, by adopting an intermediate base curve of the right and left eyes, being balance-adjusted according to the dominant eye as curvature of the first refracting surfaces of right and left spectacle lenses, it is possible to quite easily obtain spectacle lenses for spectacles excellent in performance and appearance, and having comfortable binocular vision.

BRIEF DESCRIPTION OF DRAWINGS

FIG. 5 is an order reception screen to designate types of lenses or the like when ordering a spectacle lens according to an embodiment of the present invention;

FIG. 7 is a lens design table according to example 1 of the present invention;

FIGS. 8A and 8B are astigmatism distribution diagrams from the design table in FIG. 7 according to example 1 of the present invention, in which FIG. 8A is a distribution diagram for the right eye, and FIG. 8B is that for the left eye;

FIG. 9 is a lens design table when lenses for the right and left eyes are made to be in common with the first refracting surface for the right eye according to example 1 of the present invention;

FIGS. 10A and 10B are stigmatism distribution diagrams based on the design table in FIG. 9 according to example 1 of the present invention, in which FIG. 10A is a distribution diagram for the right eye, and FIG. 10B is that for the left eye;

FIG. 11 is a lens design table when lenses for right and left eyes are made to be in common with the first refracting surface for the left eye in example 1 of the present invention to adjust balance with the dominant eye.

FIGS. 12A and 12B are stigmatism distribution diagrams based on the design table in FIG. 11 according to example 1 of the present invention, in which FIG. 12A is an astigmatism distribution diagram for the right eye, and FIG. 12B is that for the left eye;

FIG. 13 is a lens design table according to example 2 of the present invention;

FIGS. 14A and 14B are astigmatism distribution diagrams based on the design table in FIG. 13 according to example 1 of the present invention, in which FIG. 14A is a distribution diagram for the right eye, and FIG. 14B is that for the left eye;

FIG. 15 is a lens design table when lenses for the right and left eyes are made to be in common with the first refracting surface for the right eye according to example 2 of the present invention;

FIGS. 16A and 16B are astigmatism distribution diagrams based on the design table in FIG. 15 according to example 2 of the present invention, in which FIG. 16A is a distribution diagram for the right eye, and FIG. 16B is that for the left eye;

FIG. 17 is a lens design table when lenses for the right and left eyes are made to be in common with the first refracting surface for the left eye according to example 2 of the present invention;

FIGS. 18A and 18B are astigmatism distribution diagrams based on the design table in FIG. 17 according to example 2 of the present invention, in which FIG. 18A is a distribution diagram for the right eye, and FIG. 18B is that for the left eye;

FIG. 19 is a lens design table when lenses for the right and left eyes are made in common with an intermediate curve of the first refracting surfaces of the left and right eyes to balance-adjusted with the dominant eye according to example 1 of the present invention;

FIGS. 20A and 20B are stigmatism distribution diagrams from the design table in FIG. 19 according to example 1 of the present invention, in which FIG. 20A is a distribution diagram for the right eye, and FIG. 20B is that for the left eye;

FIGS. 21A, 21B, 21C, and 21D are plan views of an example of a method for measuring a dominant eye according to the present invention, in which FIG. 21A is a view showing a state of watching an object O with both eyes, FIG. 21B is a view showing a state of looking for an object O with both eyes through a hole in a shield B, FIG. 21C is a view showing a state that the right eye out of the right and left eyes is blocked with a cover C, and FIG. 21D is a view causing a shortage of sensibility to a sense of distance when a design overemphasizing the dominant eye is given.

BEST MODE FOR CARRYING OUT THE INVENTION

Figure 1:
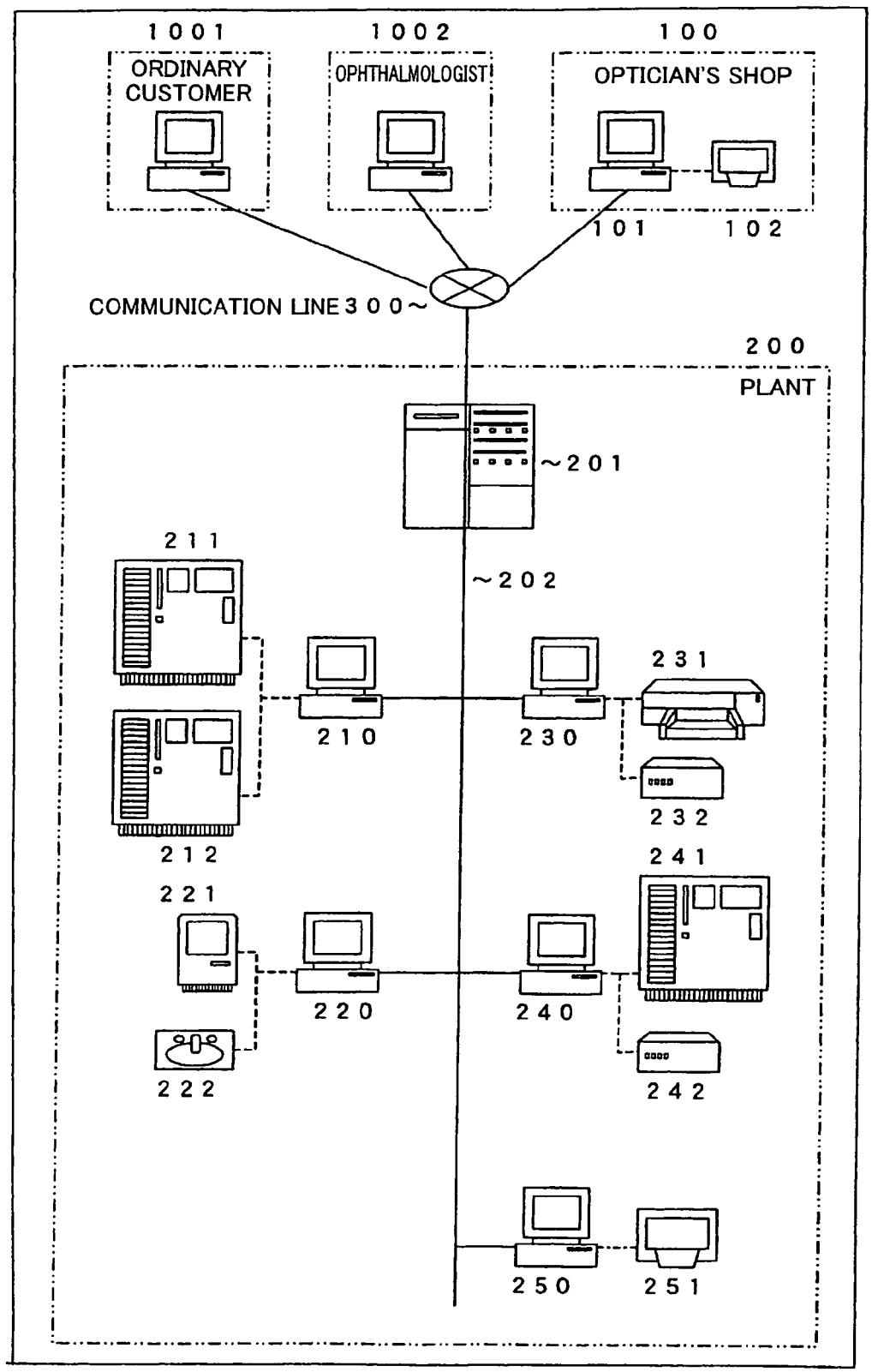
FIG. 1 is a view showing the entire structure of a system to execute a method for supplying spectacle lenses according to an embodiment of the present invention.

FIG. 1 is a view showing the entire structure of a system to execute a method for supplying spectacle lenses according to an embodiment of the present invention. In FIG. 1, an optician's shop 100 to be an orderer side and a lens manufacturer's plant 200 to be a lens processor side are connected with a communication line 300. Though only one optician's shop is shown for simplicity, actually a plurality of optician's shops are connected to the plant 200. The communication line may be connected to a general consumer 1001, or an ophthalmologist 1002 other than the optician's shops. Moreover, the communication line may be not only a public communication line but also an exclusive communication line. Furthermore, the communication line may be that using the Internet.

A customer side online computer 101 and frame shape measuring equipment 102 are disposed in the optician's shop 100. The customer side computer 101 is provided with input equipment such as a key board, mouse, and the like and a screen display unit such as a CRT, liquid crystal display, and the like, and connected to the communication line 300. Condition data necessary for machining such as spectacle lens information, prescription value, instruction for machining, and the like are inputted from input equipment such as a keyboard, mouse, and the like to the customer side computer 101, and identification numbers such as type, article number by a frame manufacturer, or spectacle frame actual measurement values by frame shape measurement equipment, as for frame data, are inputted and sent to the plant 200.

Data sent from the customer side computer 101 is transmitted on-line to a manufacture side main frame (computer) 201 of the plant 200 via the communication line 300. A relay station may be provided between the customer side computer 101 and the manufacture side main frame 201. In a case of the Internet, a browser serves the function. Note that as for a place to dispose the customer side computer 101 is not limited to the optician's shop 100.

The manufacture side main frame 201 is provided with a spectacle lens machining design program, a beveling design program, and the like, and computes a lens shape including a bevel shape based on data transmitted from the customer side computer. The result is sent back to the customer side computer 101 via the communication line 300, displayed on the screen display unit, and lens shape designing values being the computed result are transmitted to respective manufacture side computers 210, 220, 230, 240, and 250 in the plant 200 via the LAN, WAN 202.

A lens meter 221 and a thickness gage 222 are connected to the manufacturer side computer 220, and the manufacture side computer 220 compares measured values obtained with the lens meter 221 and the thickness gage 222, with lens shape designing values transmitted from the manufacture side main frame 201 to perform acceptance inspection of prescription lenses to which curvature finishing is completed and a mark (three-point mark) showing an optical center and/or a reference of layout, or a mark (paint mark) showing a dioptric power measurement position for distance vision and/or near vision of a progressive power lens is given.

A marker 231 and an image processing apparatus 232 are connected to the manufacture side computer 230, and the manufacture side computer 230 determines a blocking position to block (hold) a lens when edging and beveling are performed based on lens shape designing value transmitted from the manufacture side main frame 201, and is used to provide a blocking position mark. Using this blocking position mark as a guide, a tool for the blocking is fixed to the lens.

An NC controlled lens grinding apparatus 241 composed of a machining center and a chuck interlock 242 are connected to the manufacture side computer 240, which performs edging and beveling based on lens shape designing values transmitted from the manufacture side main frame 201.

A bevel vertex shape measuring equipment 251 is connected to the manufacture side computer 250, which compares lens shape of the beveling-finished lens measured with the shape measuring equipment 251 together with the lens shape designing values transmitted from the manufacture side main frame 201 to determine whether or not the beveling is acceptable.

Figure 2:
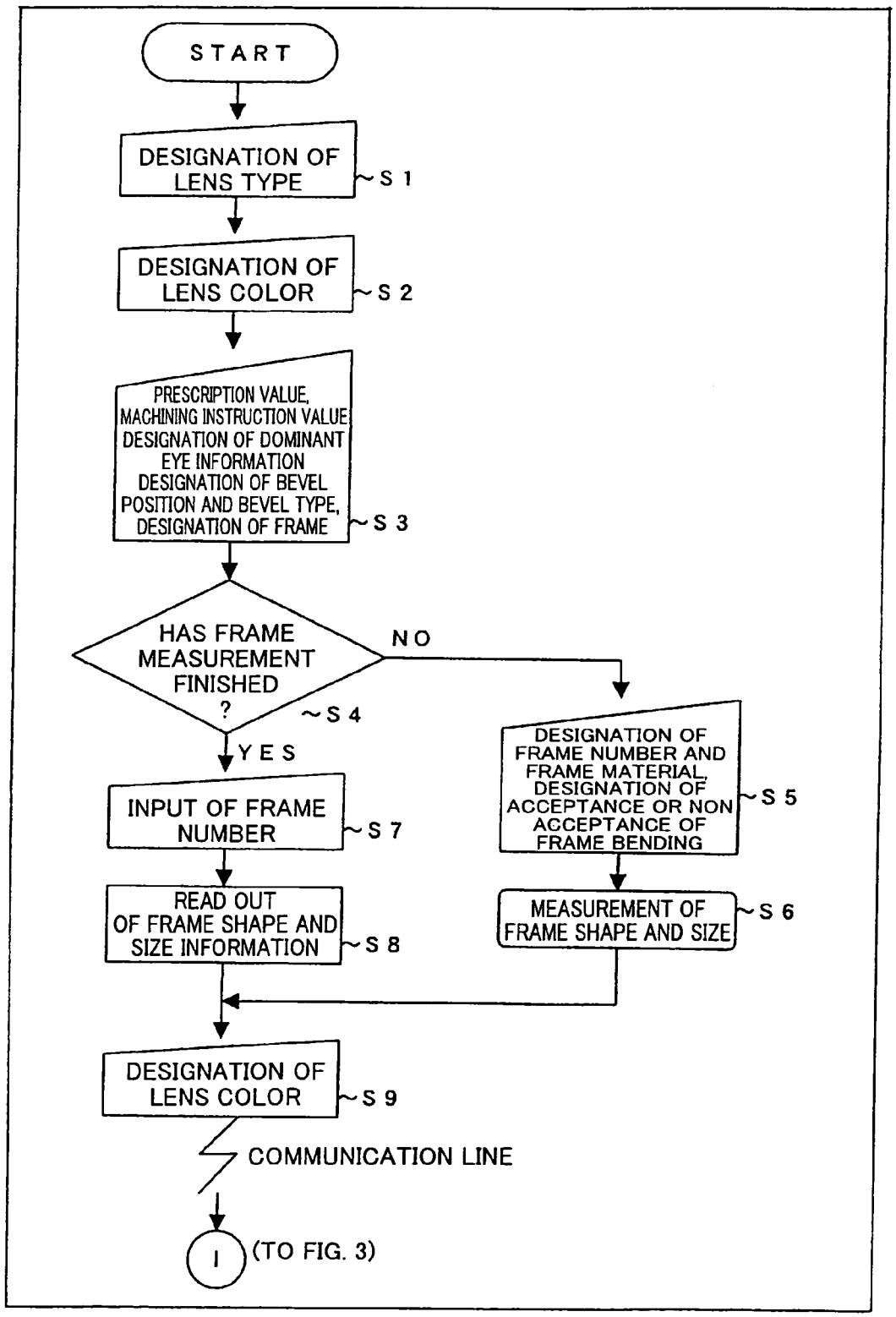
FIG. 2 is a flow chart showing a flow of the method for supplying spectacle lenses according to an embodiment of the present invention.
Figure 3:
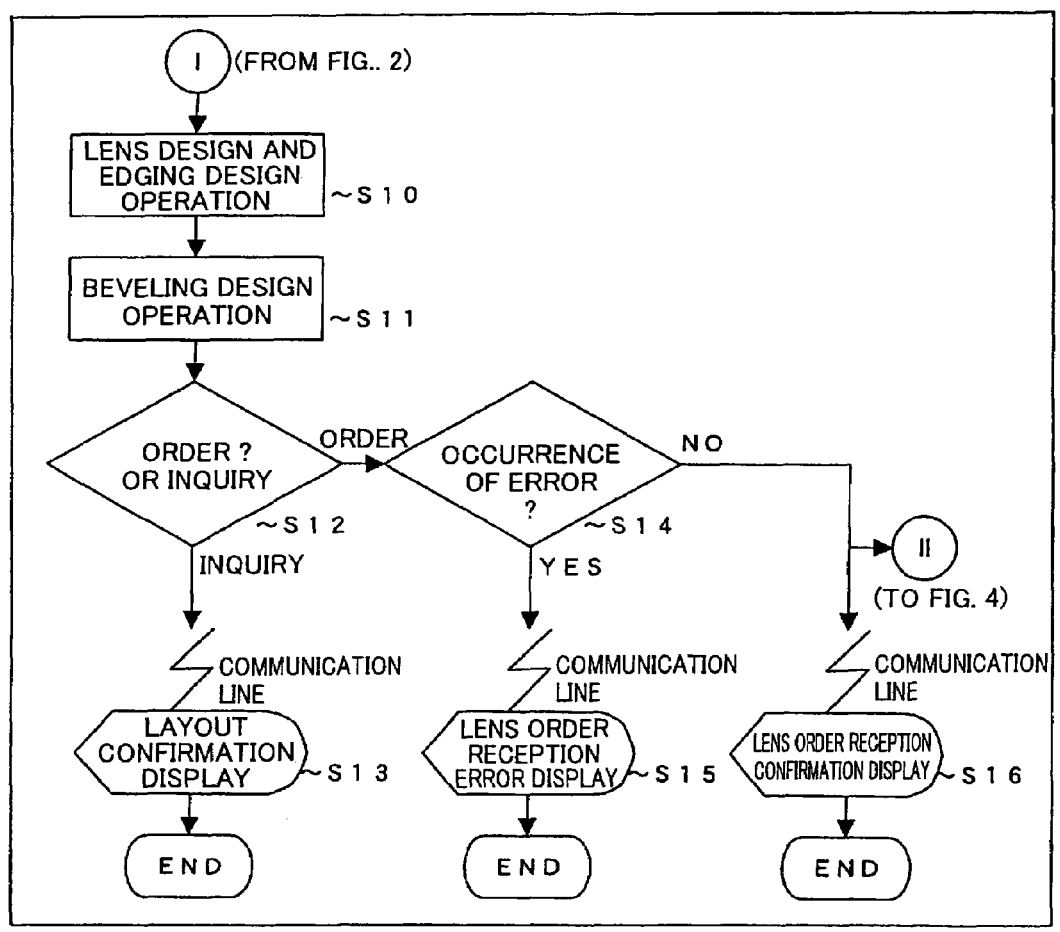
FIG. 3 is the flow chart showing a flow of the method for supplying spectacle lenses according to the embodiment of the present invention.
Figure 4:
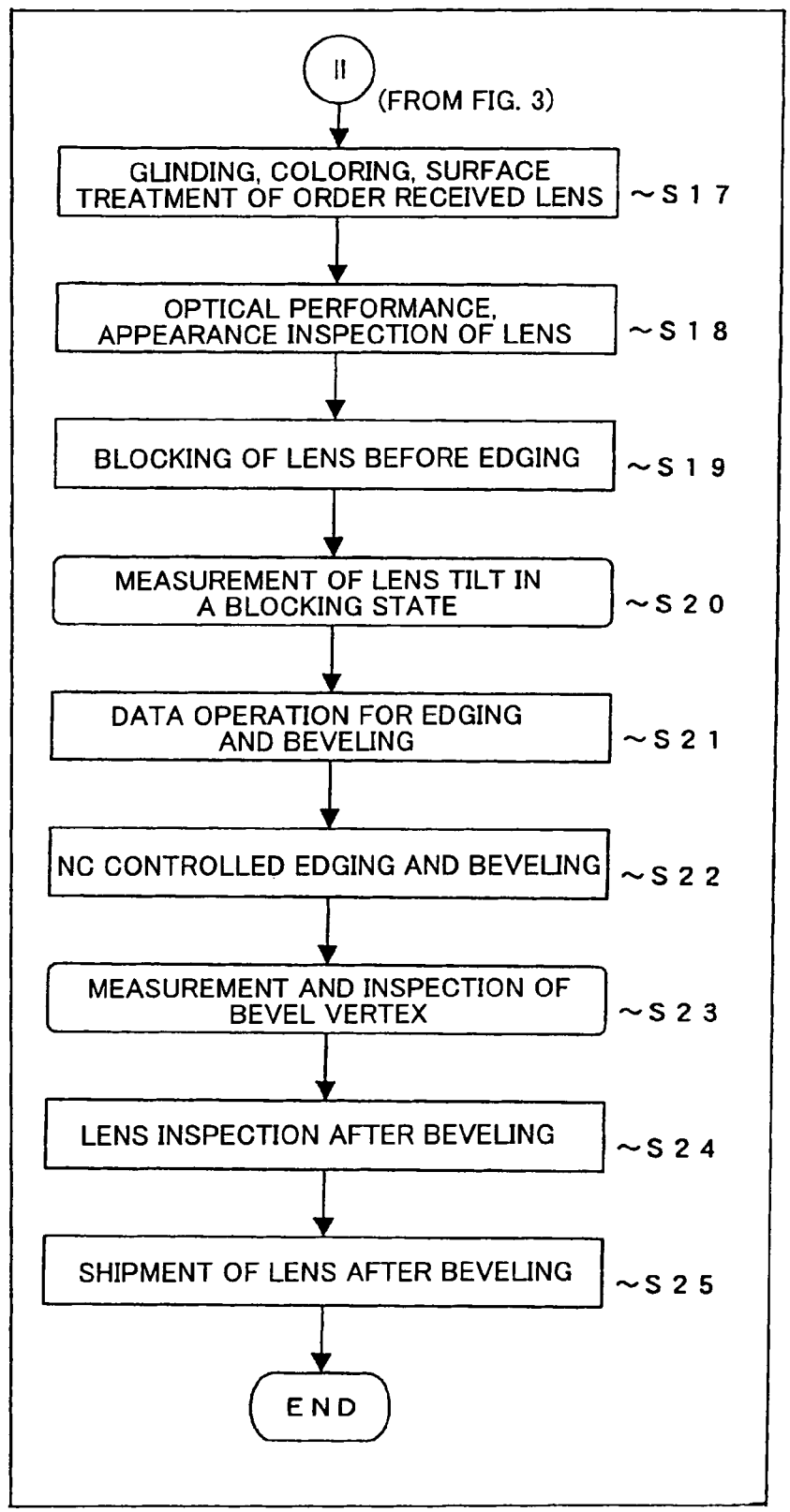
FIG. 4 is the flow chart showing a flow of the method for supplying spectacle lenses according to the embodiment of the present invention.

FIGS. 2 to 4 are flow charts showing a flow of the method for supplying spectacle lenses according to an embodiment of the present invention, FIG. 5 is a view showing an order reception screen to designate types, prescriptions, processing instructions, and the like of lenses. It should be noted that there are two types of "inquiry" and "order" in the flow of this processing, and the "inquiry" is asked by an optician's shop 100 to inform of an estimate of lens shape when lens machining including beveling is completed to the plant 200, and the "order" is requested by the optician's shop 100 to send lenses before edging and beveling, or lenses after edging and beveling to the plant 200.

FIG. 2 is a flow chart showing a flow of a first input processing in the optician's shop 100. Note that numerals following to S in the drawing indicate step numbers.

[S1] A lens order and inquiry processing program of the customer side computer 101 in the optician's shop 100 is started by a starting operation, and an order reception screen is displayed on a screen display unit. An operator in the optician's shop 100 designates a lens type to be an object to order or inquiry with input equipment such as a key board and a mouse, watching the order reception screen.

FIG. 5 is a view showing an example of an order reception screen displayed by an initiated order and inquiry processing program. The operator in the optician's shop 100 designates a lens type under item "R lens" or "L lens" in column 53. That is, a maker's product classification mark is inputted, through which lens material, refractive index, coating, lens color, and so on, and furthermore, a type of optical design if it is a progressive-power lens, can be designated. When column 51 is for inquiry, two types of lenses can be designated so that a difference between lens types can be comparatively studied. The "pattern" item in column 52 designates a lens for order or inquiry is a lens after edging and beveling (HELP) or a lens not to be edged, and not to be beveled. In an item of "METS processing" in column 52, designation of processing to adjust the thickness of a lens to a minimum requirement value for setting into a frame, or designation of processing to chamfer for making the edge of a minus-power lens unobtrusive and to grinding-finish that portion. In an item of "usage" in column 52, designation is made whether emphasis is put on recognition of space or on discrimination of an object by adjusting balance of a dominant eye according to wearing conditions or wearing purpose of the lens, namely according to the time of wearing. In this instance, though it is designated as "outdoors", it is possible to designate a situation at the time of lens wearing such as "OA work" or "driving a car" or the like, or purpose at the time of lens wearing such as "fishing" or "golfing".

In an item of "designation of a dominant eye" in column 54, it serves both for distinction of yes or no of dominant eye designation itself and designation as for which eye of the right and left eyes is a dominant eye (the eye mainly used when a person looks something) in a case of yes. When "dominant eye designation" is yes, it is handled as "dominant eye information" combined with designation of "usage" in the aforementioned column 52, which exerts influence on the spectacle lens design such as whether optical design to give preference in optical performance to either one of the right or left eyes is performed or how much weight of preference in optical performance is performed.

The "dominant eye information" works only when both of "usage" item and "dominant eye designation" item are inputted. For instance, when only "usage" item is designated, which one of the right or left eye should be preferred cannot be determined. On the contrary when only "dominant eye designation" is designated, it is impossible to design giving preference to either one of the right or left eye, because it cannot be determined whether dynamic recognition of depth in space should be emphasized or static discrimination of an object in space should be emphasized. Accordingly, in the aforementioned cases including a case of both "usage" and "dominant eye designation" items being not designated, spectacle lens design according to a base curve based on the Tscerning's ellipse, which is a standard method, is performed.

When both "usage" item and "dominant eye designation" item are inputted, for instance, when designation of the "usage" item is "outdoors" putting emphasis on dynamic recognition of depth in space, and the "dominant eye designation" is "yes" on the left eye, top priority problem in design is to take precedence over optical performance of spectacle lens for the right eye so as not to put too much emphasis on the dominant eye, and when designation of "usage" item is "OA work" putting emphasis on static discrimination of an object in space, and "dominant eye designation" is "yes" on the left eye, top priority problem in design is to take precedence over optical performance of spectacle lens for the left eye so as to put too much emphasis on the dominant eye.

Figure 21:
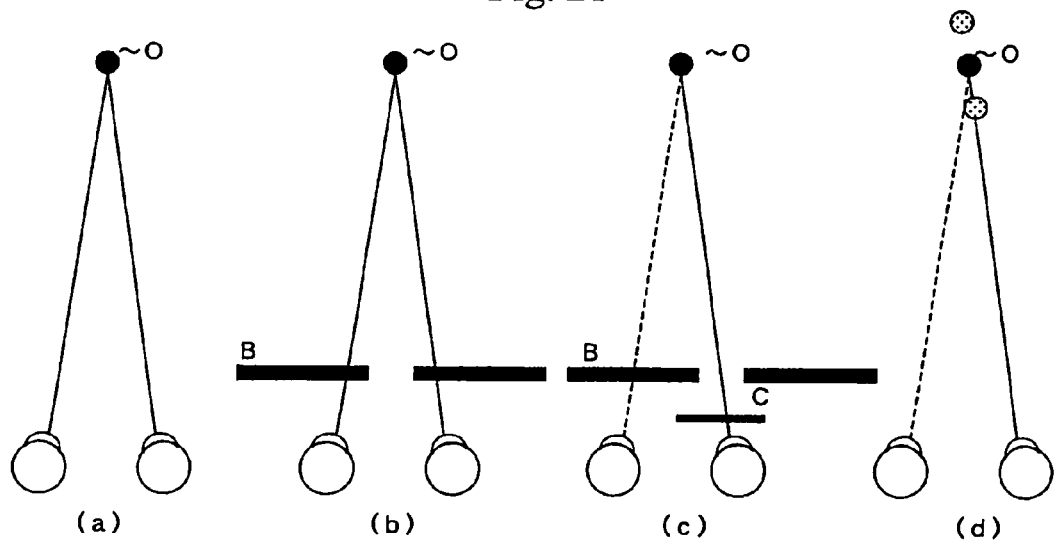

FIGS. 21A, 21B, 21C, and 21D are plan views of an example of a method for measuring a dominant eye. In FIG. 21A, an object O is watched with both eyes. In FIG. 21B, a shield B with a hole having about 5 mm in diameter is then placed at a position about 10 cm in front of a person's face, and the object O is found through the hole of the shield B keeping both eyes open. In FIG. 21C, and lastly, respective right and left eyes are covered alternately with a cover C lastly. At this time, a side of an eye losing sight of the object O out of the right and left eyes when blocked with the cover C is a dominant eye. The object O is disposed at respective positions for distance vision, intermediate vision, and near-vision to measure each dominant eye. The case of wearing spectacle lenses for which design putting too much emphasis on a dominant eye is given is, in a sense, a state shown in FIG. 21D, which causes shortage of sensibility to a sense of distance. Various methods to measure a dominant eye are known in addition to this method, the dominant eye can be measured with other methods. Though not shown, a soft key menu is displayed on a lower portion of an order reception screen in FIG. 5. Here, a "transmission key" to transmit data registered on the screen, a "registration key" to register data inputted on the screen, a "switching key" to switch between order and inquiry, a "delete key" to delete data inputted on the screen, a "page designation key" to designate a page number on the order reception screen, and further a "completion key" to complete order reception processing are displayed. These soft keys are corresponded to function keys on a key board of the customer side computer 101 and selectively designated.

[S2] Designation of a lens color is carried out in column 53 in FIG. 5.

[S3] A fundamental portion of prescription value of a lens such as spherical power, cylindrical power, a cylinder axis, addition power, and the like of the right and left eyes is inputted in column 54 in FIG. 5, and designation of processing and the like are similarly inputted in a processing item in column 54. Spectacle frame (frame) information required when HELP/METS processing is performed is inputted in column 55, and layout information at the time of setting into a frame such as PD, NPD (near PD), SEG (segment vertex position of a multifocal lens), EP (eye point) and the like, shape information of lens edge at the time of setting into a frame, ET (required minimum edge thickness for setting into spectacle frame), bevel mode, bevel shape and the like at the time of setting into a frame are inputted. It should be noted that the layout information is to designate an eye point position which is a pupil position in a frame.

In order to correspond to order using a customer side computer of an ophthalmologist and ordinary customers who have no frame measuring equipment through the Internet, a case of inputting maker's item classification number (frame item number) and a case of inputting data obtained by directly measuring a frame can be selected as spectacle frame information. Furthermore, all frame information such as a frame size, frame materials, color, shape and size, lens shape type, and the like can be inputted. When a processing form of program is "inquiry", and if designation of lens type in Step S1 is one, spectacle frame can be designated by up to two types, so that the difference in spectacle frame can be comparatively studied.

Items of "machining 1" to "machining 3" in column 54 in FIG. 5 are portions to input designation of ordinary machining or designation of special prescription values. As an machining designation value of lens, such as central thickness of lens, edge thickness of lens, decentering, lens outside diameter, effective diameter of lenticular lens, and lens convex surface curve (base curve) and the like, and as a special prescription value, such as prism amount, prism base setting, or prism horizontal amount, prism vertical amount can be inputted. In addition, an item of "dominant eye designation" serves both to distinct yes or no of the dominant eye designation itself and to designate as for which eye of the right and left eyes is a dominant eye (the eye mainly used when a person looks something) in a case of dominant eye designation is yes. In this example, though "yes" is inputted for the right eye in the item of "designation of dominant eye", any method for designating either of the right or left eye by a check box or an optional button, or by numerically designating a precedence ratio in optical performance for respective right and left eyes such as right eye 60% and left eye 40%, are adoptable.

In item of "bevel mode" in column 56 in FIG. 5, there are modes called "1:1", "1:2", "convex profiling", "frame profiling" and "auto beveling" corresponding to a place of bevel in the edge of a lens. It doesn't matter whether the selection is made from these modes or from a menu list though a number is inputted in this example. Note that "convex profiling" is a mode to set up a bevel along the lens convex surface.

Item "position" in column 56 in FIG. 5 is used when the beveling mode is "convex profiling", "frame profiling" or "auto beveling". It designates how far is the position of the bevel vertex from a lens convex surface towards a concave surface in 0.5 mm increments. Even when a spectacle frame is thick and there are some distance from the front face of the frame to the bevel groove, it is possible to place the bevel vertex so that the convex surface of the lens is along the front surface of the frame by inputting in this "position".

Selection is made from "reference bevel", "small bevel", "bevel for combi (for combination frame)", "grooving" and "flatting" in item of "bevel shape" in column 56 in FIG. 5. The "bevel for combi" is designated when an ornament member is provided on a spectacle frame, and lenses touch the ornament member. It is also selectable from a menu list, though a number is inputted in this example.

[S4] Distinction is made as for whether or not measurement of the spectacle frame shape designated in column 55 in FIG. 5 by frame shape measurement equipment 102 has already completed (whether or not shape data are obtained). If already completed (obtained), the processing is advanced to Step S7, and not completed (not obtained), the processing is advanced to Step S5.

[S5] Processing is first advanced from a lens order, lens inquiry processing program to a frame shape measurement program in the customer side computer 101 in the optician's shop 100 first. Then, a measurement number is inputted for data classification, preservation and search, on a spectacle frame of which shape and size are to be measured from now on. Material (metal, plastic, or the like) of the spectacle frame is designated, and whether or not the frame can be bent is further designated. Material for spectacle frame is used for operation in Step S11 as a parameter to compensate the circumference of the bevel vertex according to the material so that lenses are fit to a spectacle frame when the lenses are set in the spectacle frame. In a case where bending of the frame is not accepted but the lens cannot be set into the frame without bending the frame, information is made to the customer side computer 101 in the optician's shop 100 not to receive the order and the order reception error is displayed on a screen display unit.

[S6] A spectacle frame to be measured is fixed to the frame shape measurement equipment 102 to start measurement. The frame shape measurement equipment 102 allows a stylus to contact with a bevel groove in right and left rims of a spectacle frame, to rotate the stylus around a prescribed point to three-dimensionally detect cylindrical coordinate values (Rn, θn, Zn) (n=1, 2, . . . , N) of the size and shape of the bevel groove, and the measured data are transmitted to the customer side computer 101. In the customer side computer 101, smoothing of these measured data is carried out as necessary, and central coordinate values (a, b, and c) of an approximate toric surface of the spectacle frame, a radius RB along the base direction, a radius RC in the cross direction, normal vectors (p, q, r) of the toric surface, and furthermore, a frame curve CV (curvature of a spherical surface supposing that the spectacle frame is on the spherical surface), the circumference FLN of a bevel groove, frame PD (distance between centers of right and left rims of spectacle frame) FPD, frame bridge length DBL, A size/B size which is a horizontal/vertical maximum width between right and left rims of spectacle frame, frame minimum required diameter ED, and tilt angle TILT which is an angle between right and left rims of spectacle frame are calculated.

[S7] When spectacle frame has been already measured and the data are retained, a measurement number to read out the data is inputted. When spectacle frame data are supplied by a manufacturer, its item classification number (item number) of the spectacle frame is inputted.

[S8] According to the measurement number or the item classification number, data for shape and size of corresponding spectacle frame are read out from a customer side computer or a manufacture side main frame.

From the afore-mentioned Steps S1 to S8, machining condition data required for designing and manufacturing of lenses such as spectacle lens information, prescription values, dominant eye information, spectacle frame information, layout information, machining instruction information, and the like are transmitted.

[S9] Either "inquiry" or "order" is designated in column 51 in FIG. 5. Data such as lens information, prescription values, spectacle frame information, layout information, and dominant eye information, and so on obtained by execution of the above steps are transmitted to the manufacture side main frame 201 in the plant 200 through the communication line 300. The spectacle frame information includes two dimensional polar coordinate values (Rn, θn) (n=1, 2, 3 . . . , n), central coordinate values (a, b, and c) of the toric surface, a radius RB along the base direction, a radius RC in the cross direction, normal vectors (p, q, r) of the toric surface, and furthermore, a frame curve CV, the circumference FLN of a bevel groove, frame PD (distance between frame centers) FPD, frame bridge length DBL, A size/B size, frame minimum required diameter ED, tilt angle TILT and the like.

FIG. 3 is a flow chart showing a flow of processing in the plant 200, and steps of recognition and error display performed in the optician's shop 100 according to information from the plant 200.

[S10] A spectacle lens order reception system program, a spectacle lens machining design program, and a beveling design program are provided in the manufacture side main frame 201 in the plant 200. Machining condition data such as spectacle lens information, prescription values, dominant eye information, spectacle frame information, layout information, bevel information, and the like are transmitted via the communication line 300, the spectacle lens edging design program is activated through the spectacle lens order reception system program to perform operation of the lens machining design.

First, whether or not the outside diameter of a designated lens is not short to the spectacle frame is confirmed, based on prescription values of the spectacle lens, shape information of the spectacle frame, and layout information. When the outside diameter of the lens is short, shortage direction and shortage amount in a boxing system is calculated and send back the processing to the spectacle lens order reception system program to display lens order reception error on the customer side computer 101 in the optician's shop 100.

Then, the lens machining design program is executed. How to execute the lens edging design program will be explained hereinafter. Here, the case where in the afore-mentioned column 52 of the order reception screen in FIG. 5, outdoors is designated as "usage", and in column 54, the right eye is designated as "dominant eye" will be explained. Moreover, it is designed on the assumption that an object point is at an infinite distance because the spectacles are used outdoors. Furthermore, reference progressive refracting surface design in which distribution of astigmatism and distribution of curvature of field from distance vision to near-vision via intermediate vision take the best-suited arrangement according to prescribed dioptric powers for each base curve is given to a progressive power lens especially in it design, and optical factors except prescribed dioptric powers are required to be bilaterally equal. Accordingly, since a base curve of right and left spectacle lenses must be the same, a progressive power lens will be explained as an example. It is needless to say, however, that the present invention is applicable not only to a progressive power lens, but also to a single vision lens, a multifocal lens, and the like.

Hereinafter, the basic structural portion of an optical design method for the progressive power lens will be briefly explained, and the present invention will be also explained.

First, reference progressive refracting surfaces are determined according to respective prescriptions for the right and left eyes. In the lens machining design program, a convex surface and a concave surface of the reference progressive refracting surfaces are set as a functioned surface by a prescribed expression. Since the present invention is not related to progressive power lens surface design, a detailed explanation of making functional or the like will be omitted. And in such a case, the afore-mentioned reference progressive refracting surface is set by determining dioptric power distribution over the entire surface of spectacle lens in respective areas of distance vision, intermediate vision, and near vision. As a factor to determine the afore-mentioned dioptric power distribution, there are a base curve value to satisfy a prescribed dioptric power for distance vision, addition power, dioptric power distribution in the horizontal direction in distance vision area and near-vision area, arrangement of distance vision and near-vision areas on the spectacle lens, distribution of dioptric power change in a progressive corridor, arrangement of a principal sight line, arrangement of astigmatism distribution, distribution of curvature of field, and the like, and the dioptric power distribution is determined by these factors.

Next, a progressive refracting surface is determined by performing optimization calculation to the reference progressive refracting surfaces determined for the right and left eyes respectively. The optimization calculation determines prescribed concrete dioptric powers which are used as input data for design. Based on the design input data, the shape and size of the lens curve surface is determined, and the lens optical characteristics are found by a ray tracing method. Since the ray tracing method itself is a well-known technique, a detailed explanation thereof will be omitted. When explained briefly, a center of rotation is first established as a start point of the ray tracing. Tracing points on a lens surface to perform ray tracing are established on the entire surface of the lens. Though, the more the numbers of established points, the more accurate design can be performed, but time necessary for operation processing is also proportionally increased, it must be handled with care. For each ray which is emitted to pass through the afore-mentioned established tracing point on the lens surface and to pass a convex surface and a concave surface of the spectacle lens, prescribed optical factors (astigmatism, curvature of field, distortion aberration, and the like) are calculated. For instance, when a ray tracing area is a near-vision area, a temporary optical model in a wearing state is sometimes established based on a prescribed near object distance (near work target distance: distance to near targeted operation) and positions of the right and left eyes, a VR value (a distance from the center of rotation of the eye to the lens surface), distance vision PD, frame data, frame forward tilt to perform ray tracing operation. Its optical characteristics are evaluated from the prescribed optical factor (astigmatism, curvature of field, distortion aberration or the like) using the afore-mentioned reference progressive refracting surface as an initial value, and while various design factors to be explained hereinafter are being handled based on the evaluation result, candidates of a progressive refracting surface are listed, and when the optical factor gets equal to or less than the prescribed set up value, the optimization calculation is finished to determine a progressive refracting surface (base curve).

In the present invention, while performing weighting of design factors, especially such as identification of lens area (distance vision area, intermediate vision area, near-vision area, and the like) and designation of optical amount (astigmatism, curvature of field, distortion aberration, and the like on the surface or in transmitting) by balance adjustment of dominant eye information (combination of usage condition, functional condition of the spectacle lens, physical requirement of a person who wears spectacles or the like), the optimization calculation is performed by changing the merit function on which weight of optical amount along respective rays is applied. For instance, when usage requirement needs dynamic recognition of depth in space, functional requirement is from distance vision to near vision, and physical requirement is for the right eye, optical performance of a spectacle lens for the left eye takes precedence, and since dynamic recognition of depth in space is importance in a distance vision area, a degree of precedence in optical performance of spectacle lens for the left eye affects greatly, while on the contrary, in a near-vision area, since static discrimination of an object in space is important, a degree of precedence in optical performance of spectacle lens for the left eye affects less. Then, when ratio of optical amount of right and left eyes comes equal to or less than a targeted established optical amount, the optimization calculation is finished.

Figure 22:
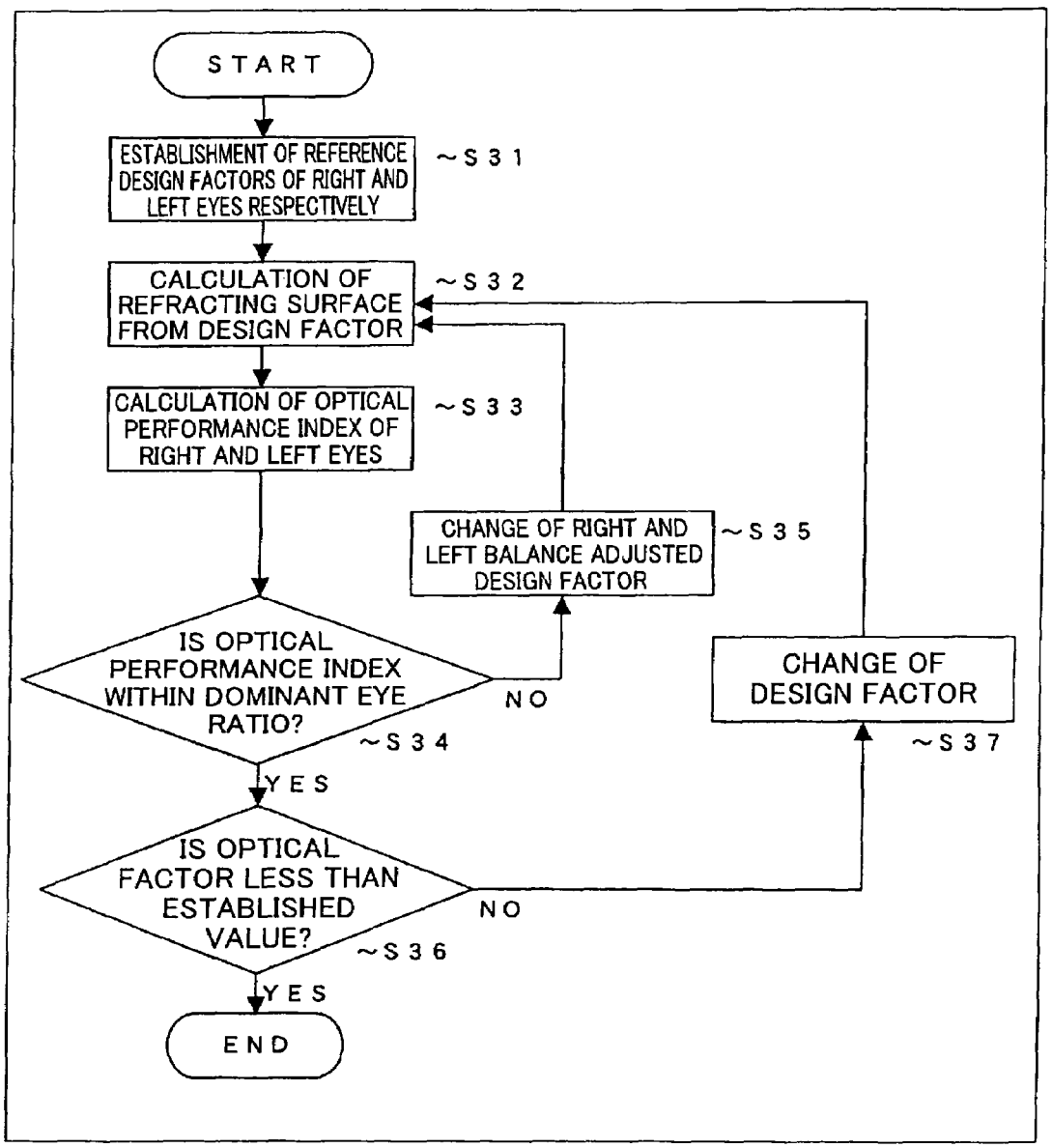
FIG. 22 is a flow chart showing a rough flow of spectacle lens design planning to perform balance adjustment of a dominant eye according to an embodiment of the present invention.

FIG. 22 is a summarized flow chart of lens design according to balance adjustment of dominant eye information.

[S31] A reference design factor of a spectacle lens according to each prescribed dioptric power for each right or left eye is established individually.

[S32] A refracting surface is designed according to established design factors. In a case of conventional design methods, the process advances to Step S36.

[S33] An optical performance index of a spectacle lens for each right or left eye is calculated.

[S34] The optical performance index of the spectacle lens for each right or left eye is judged whether it is within a permissible range in dominant eye ratio. If it is in a permissible range, the process advances to Step S36.

[S35] Any one of the design factors is changed within a range of balance adjustment of dominant eye information, and the process returns to Step S32.

[S36], Judgment is made as to whether or not an optical factor of spectacle lens of each right or left eye is in a permissible range. If it is in the permissible range, design of a refracting surface is finished.

[S37] Either of design factors is changed, and the process returns to Step S32.

Figure 6:
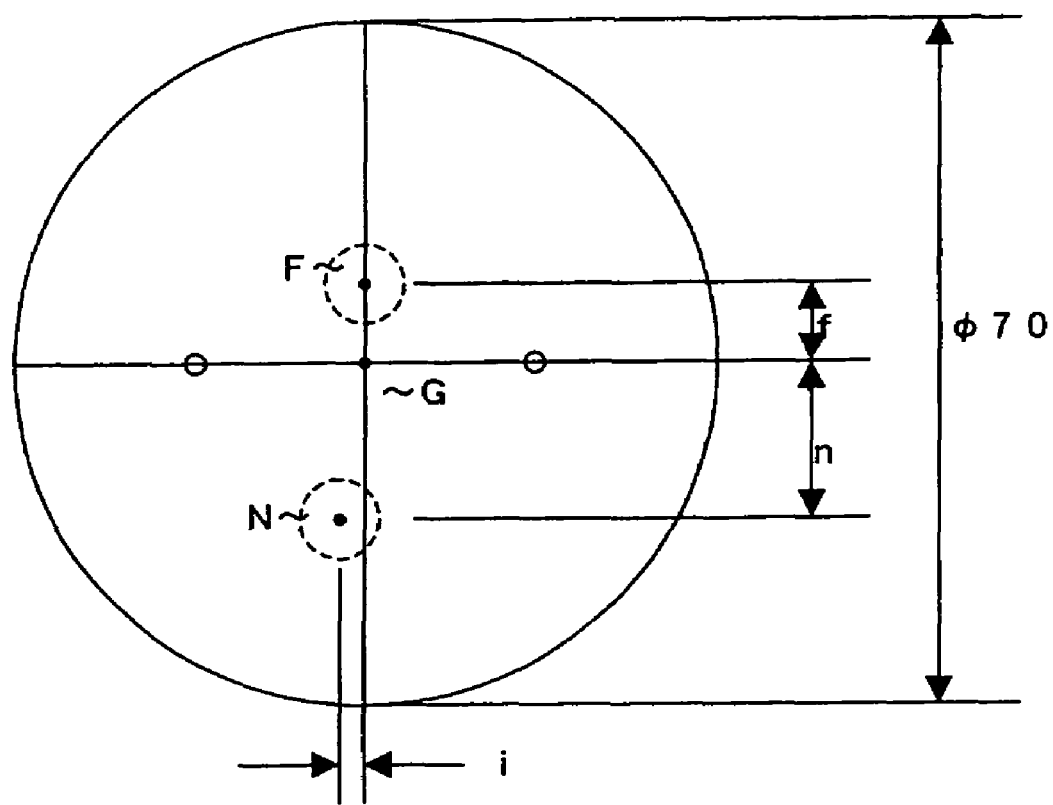
FIG. 6 is an explanatory view of a progressive power lens for the left eye having a diameter of 70 φ according to an embodiment of the present invention seen from an object side.

FIG. 6 is a view showing a progressive power lens for the left eye seen from a first refracting surface side (object side). In FIG. 6, the principal sight line reaches near-vision point N positioned at a distance n downward of geometrical center G and inward i of bridge side from distance vision point F positioned at a distance f upward of geometrical center via the geometrical center G which is a half way portion of intermediate vision progressively varied. The principal sight line varies to get the best suited path depending on visual acuity and addition power. Hereinafter, some concrete prescription examples are listed, and examples to design by applying a method of the present invention in such a case will be explained comparing with a case of applying the conventional methods.

EXAMPLE 1

The prescription of this example is such that the left eye is +4 D, the right eye is +5 D, and addition power of right and left eyes is 2 D. The dominant eye information says that the usage is to wear outdoors, and the right eye is designated as a dominant eye. Therefore, since dynamic recognition of depth in space is an important design requirement in this example, at the time of balance adjustment, optical performance of a spectacle lens on the side of not dominant eye, that is, on the side of a spectacle lens for the left eye is given a high priority. According to conventional lens design methods, a lens design table (lens data table) prepared according to previously prescribed dioptric power is selected, and design using the value in the table is accomplished. FIG. 7 is a table showing a lens data table for reference progressive refracting surfaces according to prescribed dioptric powers for respective right and left eyes selected in the case of the prescription in example 1.

Figure 8:
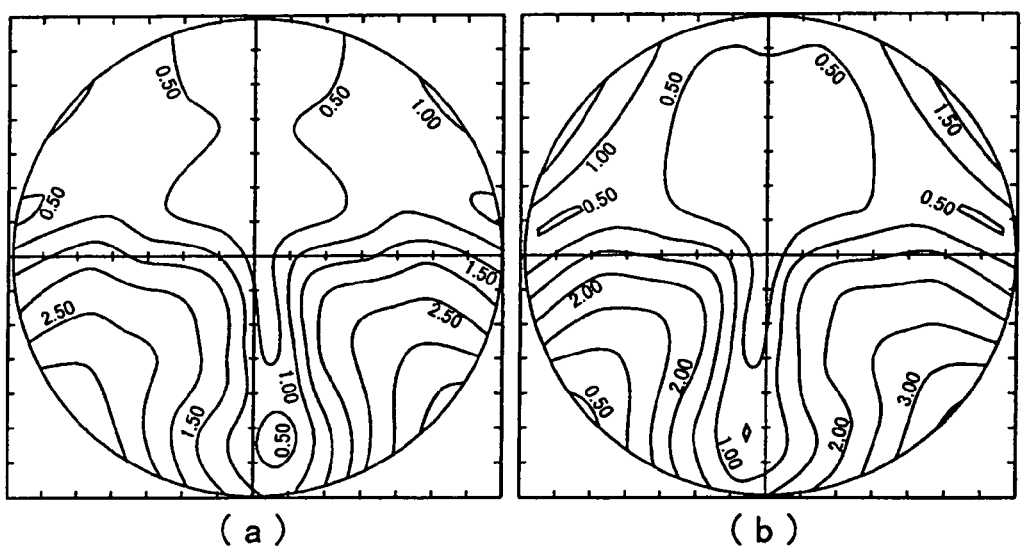

FIGS. 8A and 8B are views showing astigmatism among optical performance of lenses designed according to a lens data table shown in FIG. 7, in which the first refracting surfaces are reference progressive refracting surfaces of respective right and left eyes. FIGS. 8A and 8B are astigmatism distribution diagrams in which FIG. 8A is that for the right eye and FIG. 8B is that for the left eye, representing in contour by every 0.5 D. The contour line is in common with distribution diagrams to be explained below. Sensibility of a human eye to astigmatism is most sensitive to distance vision, and tendency to become dull is recognized as shifting from intermediate vision to near-vision. It is known that a distinct vision field in distance vision is required to be astigmatism within about 0.5 D, and a distinct vision field can be ensured when in near-vision, if astigmatism is from about 0.75 D to 1.0 D.

As described above, for a progressive power lens, especially in designing of its progressive surface, designing of a reference progressive refracting surface is given so that arrangement of astigmatism from distance vision to near-vision through intermediate vision and arrangement of distribution of curvature of field for every base curve can be best suited according to prescribed dioptric powers, and optical factors except prescribed dioptric powers must be equal in right and left eyes. Accordingly, it is absolutely necessary to make the first refracting surfaces (base curve) of right and left spectacle lenses the same. According to conventional lens design methods, since the larger the curvature of a base curve, the more astigmatism is improved to visual acuity in a practical range as a spectacle lens by aforementioned Scherning's ellipse, usually either one having a larger base curve curvature out of right and left spectacle lenses is used as the one remained. FIG. 9 is a lens data table when a first refracting surface of the right eye larger in curvature of the first refracting surface out of right and left eyes is made the same as the first refracting surface of the left eye according to the aforementioned conventional lens design methods.

Figure 10:
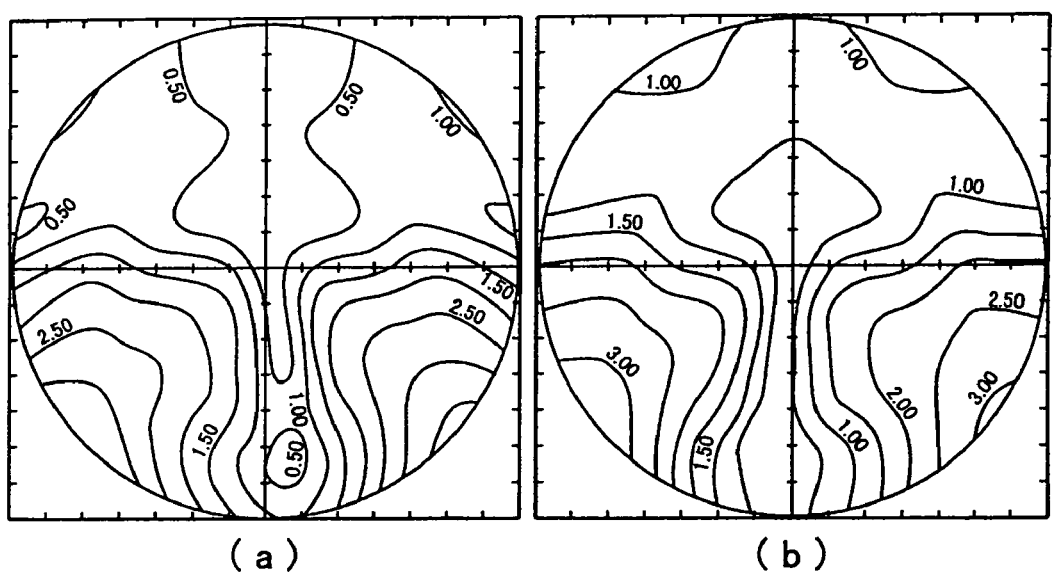

FIGS. 10A and 10B are views showing astigmatism among optical performance of a lens designed according to a lens data table in which a first refracting surface is made common with a reference progressive refracting surface of the right eye having a larger curvature of the first refracting surface out of right and left eyes in FIG. 9. FIG. 10A is a view showing astigmatism distribution of the right eye. FIG. 10B is that of the left eye. According to the conventional lens design methods, lens shape design is completed here and lens processing design and beveling design are continued.

However, when paying attention to astigmatism distribution diagram for the left eye in which dominant eye is not designated, the astigmatism distribution diagram in FIG. 10B based on the conventional design methods is found that a distinct vision field in distance vision becomes narrower with lowering in optical performance, when compared with astigmatism distribution diagram in FIG. 8B from a lens data table based on the prescribed dioptric power. A dominant eye ratio I(Dmj, Br):I(Dmn, Br) in distance vision in astigmatism distribution diagrams for both the right and left eyes in FIGS. 10A and 10B is approximately 6:4. Namely, the right eye being a dominant eye is superior in optical performance of spectacle lens than that of the left eye being a non-dominant eye, and it is easily fallen into a state of attaching too much importance to the right eye being a dominant eye, which does not suit for a usage condition as outdoor wearing which requires dynamic recognition of depth in space. Therefore, the conventional design methods cause overemphasizing of balance for a dominant eye, which brings a bad influence upon visual acuity of binocular vision due to narrowing of viewing field, lowering of sensibility to a sense of distance, and the like. Accordingly, in order to give high priority to optical performance of the left eye being not a dominant eye, the first refracting surfaces of the right and left eyes are planed to be the same with each other by using the first refracting surface of the left eye.

Figure 12:
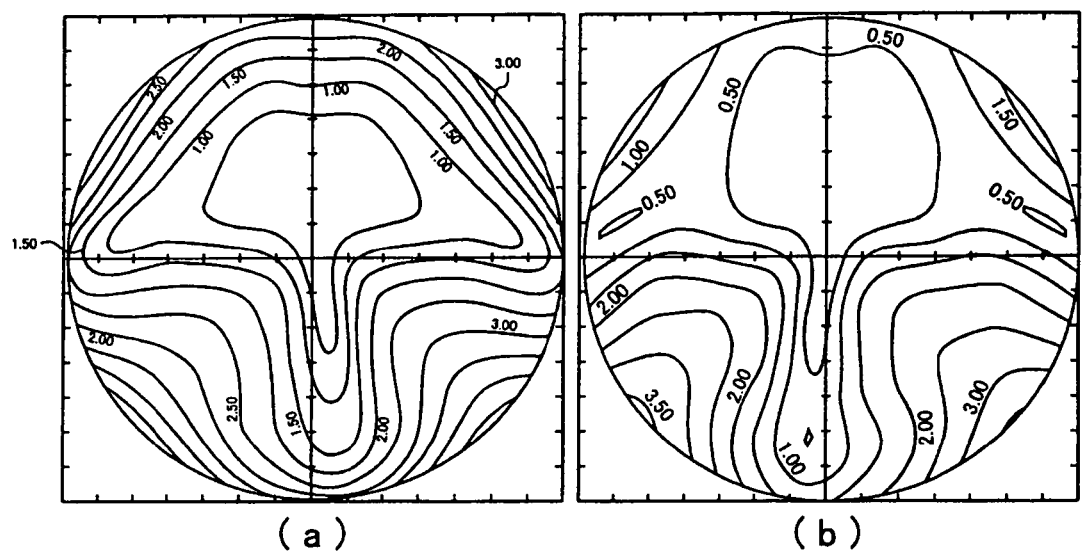

FIG. 11 is a lens data table when the first refracting surface of the left eye is made the same as the first refracting surface of the right eye to give high priority to optical performance of the left eye being a non-dominant eye. FIGS. 12A and 12B are views showing astigmatism among the optical performance of lenses designed according to a lens data table in which the first refracting surfaces in FIG. 11 are made common with a reference progressive refracting surface of the left eye in order to give high priority to the optical performance of the left eye being a non-dominant eye. FIG. 12A is an astigmatism distribution diagram for the right eye. FIG. 12B is an astigmatism distribution diagram for the left eye. The dominant eye ratio I(Dmj, B1):I(Dmn, B1) in distance vision in the astigmatism distribution diagrams for the right and left eyes in FIGS. 12A and 12B is approximately 3:7. Accordingly, a spectacle lens for the non-dominant left eye is superior in optical performance of a spectacle lens than those of the dominant right eye, and field of view through the spectacle lenses are in a balanced state between both of the left and right eyes and this state is suitable for wearing outdoors as a usage which requires dynamic recognition of depth in space. In other words, it becomes a state of balance adjusted for a dominant eye, which gives good influence on visual acuity of binocular vision. Moreover, when establishing an optical performance index, the present invention mainly uses exponentiation of spatial width of a distinct vision field in optical performance, it is also possible to establish, for instance, by adding evaluation factors caused by other optical aberration, within a range not deviating from the present invention including a method of expression.

EXAMPLE 2

Figure 14:
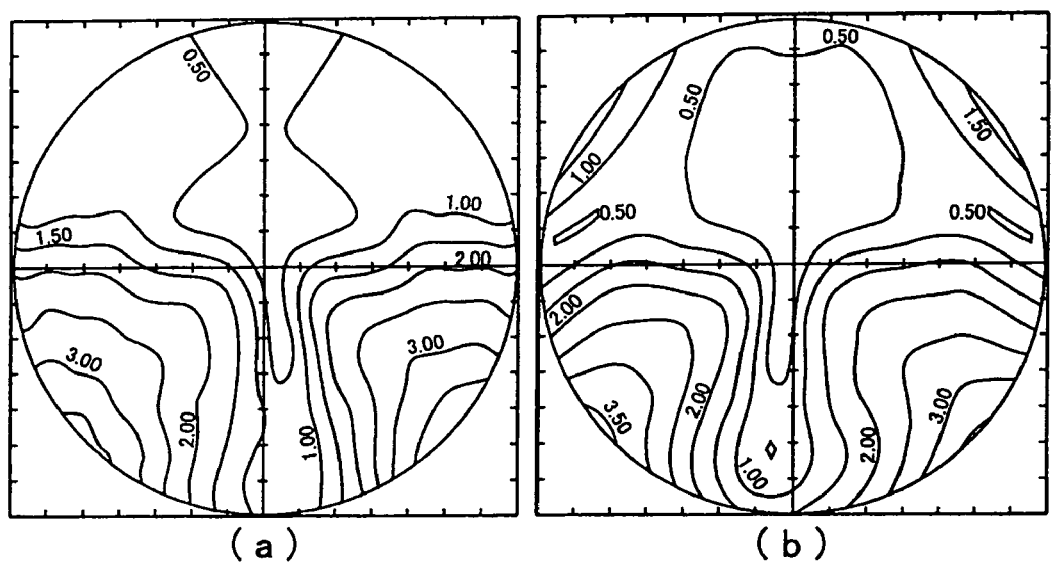

The prescription of this example is such that the left eye is +4 D, the right eye is +6 D, and addition power for both of the right and left eyes is 2 D. The dominant eye information says that the usage is wearing in a theater, and the left eye is designated as a dominant eye. Therefore, since static discrimination of an object in space is an important design requirement in this example, at the time of balance adjustment, optical performance of a spectacle lens on the side of dominant eye, that is, on the side of a spectacle lens for the left eye is given a high priority. According to conventional lens design methods, a lens design table (lens data table) prepared according to previously prescribed dioptric power values is selected to accomplish design using the value in the table. FIG. 13 is a table of a lens data for reference showing progressive refracting surfaces according to prescribed dioptric power values for respective right and left eyes selected in the case of the prescription in example 2. FIGS. 14A and 14B are views showing astigmatism among optical performance of lenses designed by following a lens data table along a reference progressive refracting surfaces according to the dioptric power of the prescription of respective right and left eyes in FIG. 13. FIG. 14A is the astigmatism distribution diagram for the right eye, and FIG. 14B is that for the left eye.

Figure 16:
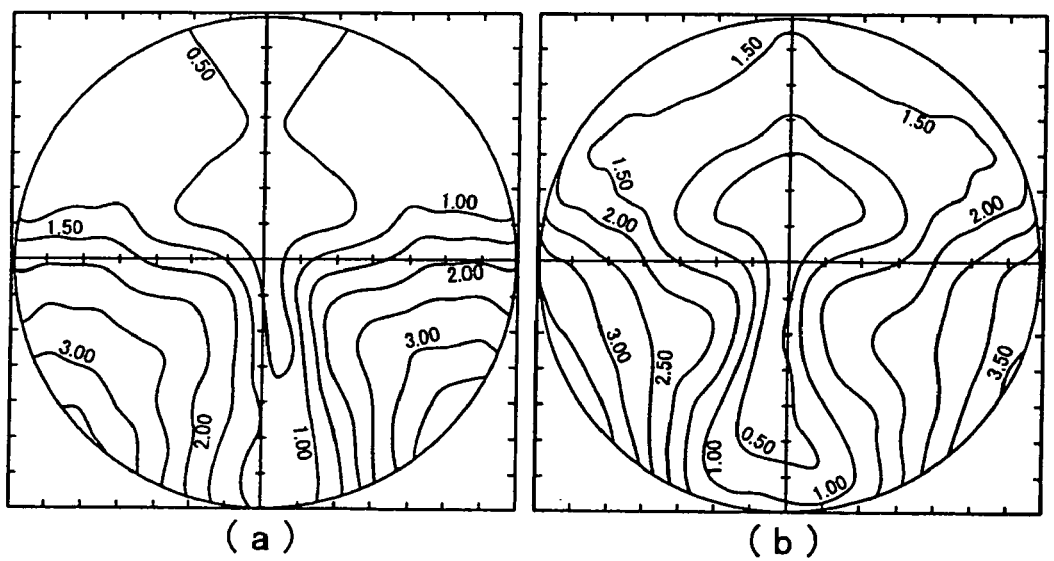

Next, according to the afore-mentioned conventional lens design methods, the first refracting surface of the right eye, which has the larger curvature out of the first refracting surfaces of the right and left eyes is made common with the first refracting surface of the left eye. FIG. 15 is a lens data table in the case of making the first refracting surface of the left eye the same as the first refracting surface of the right eye having the larger first refracting surface curvature. FIGS. 16A and 16B are views showing astigmatism among optical performance of a lens designed according to a lens data table in which a first refracting surface is made common with a reference progressive refracting surface of the right eye having a larger curvature of the first refracting surface out of right and left eyes in FIG. 15. FIG. 16A is a view showing astigmatism distribution of the right eye. FIG. 16B is that of the left eye. As described above, according to the conventional lens design methods, lens shape design is completed here and lens processing design and beveling design are continued.

However, when paying attention to an astigmatism distribution diagram of the left eye in FIG. 16B, the eye being designated as a dominant eye, it is recognized that a range of astigmatism within 0.5 D which is a distinct vision field in distance vision is narrower compared with an astigmatism distribution diagram in a lens data table according to prescribed dioptric powers in FIG. 14B. A dominant eye ratio I(Dmj, Br):I(Dmn, Br) of distance vision in the astigmatism distribution diagrams of right and left eyes in FIGS. 16A and 16B is approximately 1:9. In other words, the right eye being not a dominant eye surpasses the left eye being a dominant eye in optical performance of spectacle lens, which results in watching a stage or a screen with the right eye which is not a dominant eye. Therefore, this situation does not satisfy the usage condition designating wearing in a theater where static discrimination of an object in space is required. Accordingly, in order to give high priority to optical performance of the left eye being a dominant eye, the first refracting surfaces of right and left eyes are planed to be in common with each other by using the first refracting surface of the left eye.

FIG. 17 is a lens data table when the first refracting surface of the left eye is made common with the first refracting surface of the left eye to give high priority to optical performance of the left eye which is a dominant eye. Giving high priority to the left eye and making a curvature of the first refracting surface of the right eye small means a curvature of a refracting surface of the second refracting surface also becomes small. Therefore, it is needless to say that when a dioptric power in the prescription is positive dioptric power, care must be taken lest the second refracting surface should become a convex shape, which is not permissible as a spectacle lens.

Figure 18:
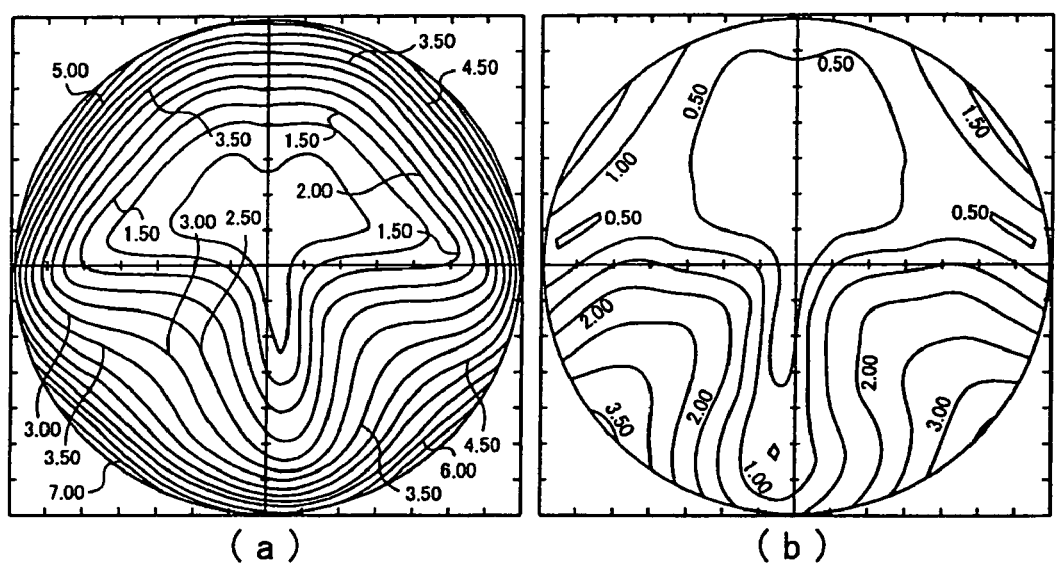

FIGS. 18A and 18B are a view showing astigmatism among optical performance of a lens designed according to a lens data table in which the first refracting surface in FIG. 17 is made common with a reference progressive refracting surface of the left eye to give high priority to optical performance of the left eye which is a dominant eye. FIG. 18A is an astigmatism distribution diagram for the right eye. FIG. 18B is an astigmatism distribution diagram for the left eye. A dominant eye ratio I(Dmj, B1):I(Dmn, B1) in distance vision in the astigmatism distribution diagrams of right and left eyes in FIGS. 18A and 18B is approximately 8:2. Accordingly, when a spectacle lens for the dominant left eye is superior in optical performance to that for the non-dominant right eye, a stage or a screen has to be watched with the dominant left eye. This situation satisfies the usage condition designating wearing in a theater where static discrimination of an object in space is required. However, the dominant ratio of about 8:2 places too much emphasis on precedence, over prioritizing the dominant eye, which might result in difficulty of binocular vision.

Then, in the lens data table according to the prescribed dioptric power of FIG. 13, the first refracting surface of the left eye and the first refracting surface of the right eye are communalized by an intermediate value of the first refracting surface of the left eye and the first refracting surface of the right eye, with the first refracting surface of the left eye set as an initial value, and redesigning is repeatedly performed until a dominant eye ratio of right and left eyes gets within a prescribed range. FIG. 19 is a lens data table in which the first refracting surface is an intermediate value obtained by redesigning.

Figure 20:
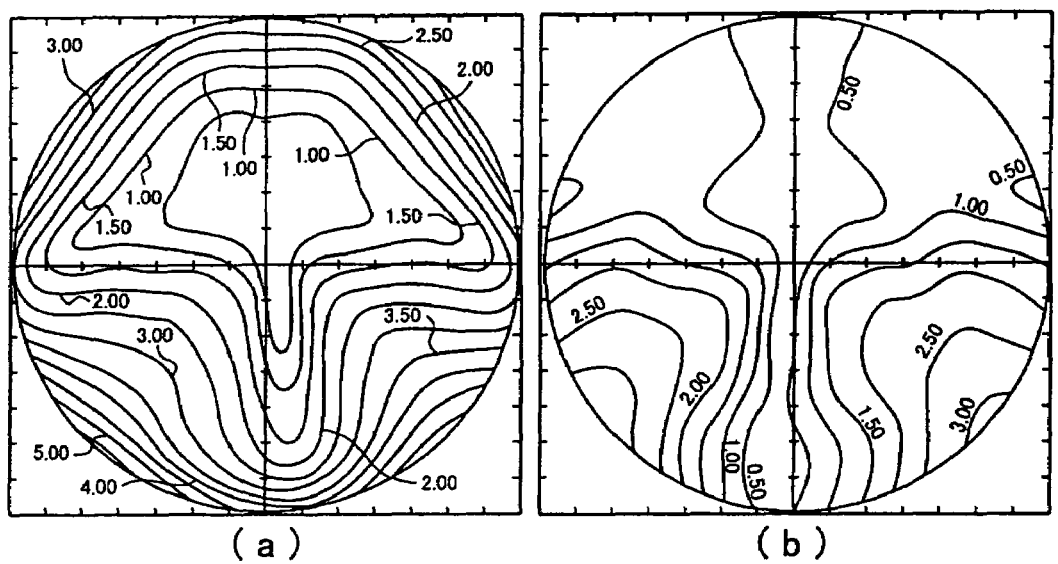

FIG. 20 is a view showing astigmatism among its optical performance of a lens designed according to a lens data table in which the first refracting surfaces in FIG. 19 are repeatedly redesigned to be an appropriate dominant eye ratio. FIG. 20A is an astigmatism distribution diagram for the right eye. FIG. 20B is an astigmatism distribution diagram for the left eye. Although lowering of optical performance of the dominant left eye is not avoidable when compared with the astigmatism distribution diagram based on the lens data table according to a prescribed dioptric power in FIG. 14B, the dominant eye ratio I(Dmj, Bi):I(Dmn, Bi) in distance vision in the astigmatism distribution diagrams of the right and left eyes in FIGS. 12A and 12B is approximately 7:3. Accordingly, a spectacle lens for the left dominant eye is superior in optical performance to those of the right eye which is a non-dominant eye, a stage or a screen has to be watched with the left dominant eye. This situation is fitted to a usage condition designating wearing in a theater where static discrimination of an object in space is required. Needless to say, a dominant ratio is also suitable, and moderate binocular vision can be provided.

Although a progressive power lens is used in the aforementioned examples as a case, it is needless to say that balance adjustment of a dominant eye ratio can be performed to a single vision lens as well as to a multifocal lens.

As above, the entire shape of a lens before edging is designed. Here, an edge thickness of the perimeter is measured at every radial for each direction of a spectacle frame to confirm that there is no portion where the edge thickness falls short of that required for framing. Then processing instruction values necessary for lens processing are calculated for the manufacture side computer 210 in the plant 200.

[S11] Next, in the manufacture side main frame 201, the beveling design program is activated through a spectacle lens order reception system program to perform the beveling calculation operation. An original point for processing to be a yardstick at the time of holding a lens to perform beveling and an axis for processing to be an axis of rotation are determined, lens processing design data up to the present is coordinate transformed into this coordinate for processing, and design operation of three-dimensional beveling is performed.

[S12] When an input operation in Steps S1 to S9 in FIG. 2 is "order", the step advances to Step 14, and when it is "inquiry", a result of the inquiry is returned to the customer side computer 101 via the communication line 300, and the process advances to Step S13.

[S13] This step is provided for displaying a dominant eye balance overemphasizing design, a dominant eye balance adjusted design conversely, or a lens estimated shape at the completion of beveling on a screen display unit based on the inquiry result returned from the manufacture side main frame in the plant 200 to confirm whether there is any problem with the spectacle lens.

A display device is provided in dominant eye balance design to compare a lens shape before adjusting the balance and data with a lens shape after the balance adjustment. Thus, lens shapes before and after balance adjustment and the like are confirmed on this display screen in the optician's shop 100 to change designation as necessary.

[S14] If designation in step S1 to S9 in FIG. 2 is "order", this step is performed, and in the processing design operation of steps 10 and 11 in FIG. 3, occurrence of errors is discriminated. When errors occur, the result is returned to the customer side computer 101 in the optician's shop 100 via the communication line 300, and the step advances to Step S15. On the contrary, when no error occurs, the result is returned to the customer side computer 101 in the optician's shop 100 via the communication line 300, and the process advances to Step S16 and at the same time advances to Step S17 and later (FIG. 4) to perform the lens processing.

[S15] In this step, since an ordered lens has encountered some troubles during a lens processing design operation or a beveling design operation, namely, a lens which cannot be processed, a display expressing a lens order reception error such as "your order is unacceptable" or the like is displayed on the customer side computer 101 in the optician's shop 100.

[S16] In this step, since an ordered lens has no trouble in a lens processing design operation or a beveling design operation, a display for confirmation of lens order reception such as "your order has been accepted" or the like is displayed on the customer side computer 101 in the optician's shop 100. Through this step, the optician's shop can confirm an order for a lens before edging or after beveling to be able to reliably frame into a spectacle frame.

FIG. 4 is a flow chart showing actual processes such as polishing, polishing of either one of the surfaces of the front or back, or both surfaces of the front and back of the lens, edging of the lens, and beveling performed in the plant 200.

[S17] From this step on, steps are carried out only when the designation from Steps S1 to S9 in FIG. 2 is "order", and no trouble has been found in the operation of lens machining design as well as beveling design. Namely, the result of the lens machining design operation in Step S10 has been transmitted in advance to the manufacture side computer 210 in FIG. 1, and curved surface finishing on either of front surface or rear surface or both is performed with a rough edger 211 and a sand polisher 212 according to the transmitted operation result. Moreover, though not shown, processing before edging such as coating/surface treatment with a coating/surface treatment apparatus is carried out. Note that when a stored lens is designated, this step is skipped.

[S18]

A quality inspection such as optical performance inspection, and outward appearance check is carried out to the spectacle lens processed so far as before edging by execution of Step S17. A manufacture side computer 220, a lens meter 221, and a thickness gage 222 in FIG. 1 are used for this inspection, and a mark (three-point mark) indicating a reference of optical center and layout, or a mark (paint mark) indicating a distance vision and near vision dioptric power measurement position of a progressive-power lens is given to an accepted lens. When an order of a spectacle lens before edging is received from an optician's shop 100, an accepted spectacle lens after the aforementioned quality inspection is shipped to the optician's shop 100.

[S19] Based on the result of the beveling design operation at Step S11, a blocking tool for lens holding is fixed at a prescribed position of the aforementioned accepted lens using a manufacture side computer 230, a marker 231, an image processor 232, and the like in FIG. 1.

[S20] The lens fixed to the blocking tool is mounted on a lens grinder 241 in FIG. 1. In order to grasp the lens position (tilt) in a state of being mounted on the lens grinder 241, previously designated, at least three positions on either front or rear surface of the lens are measured. The measured values obtained here are stored to use as operational data of Step S21.

[S21] The manufacture side main frame 201 performs beveling design operation in Step S11 again. However, in this actual edging design operation, since the theoretical lens position grasped by calculation may deviate from the actual lens position fixed by the blocking tool, compensation of this deviation is performed at the time of completing coordinate transformation to a processing coordinate. The similar operation to that for the beveling design operation in Step S11 is performed except the operation for the compensation of this deviation to calculate the final three-dimensional bevel vertex shape. Based on this calculated three-dimensional bevel vertex shape, the three-dimensional processing locus data on a processing coordinate at the time of grinding with a grinder having a prescribed radius is calculated.

[S22] The processing locus data calculated in Step S21 is transmitted to the NC controlled lens grinder 241 via the manufacture side computer 240. The lens grinder 241 includes a rotary grinding wheel for grinding, which is shifted under control in the Y-axis direction (perpendicular to the direction of the spindle shaft) to perform lens edging and lens beveling, and performs beveling while controlling the rotational angle (rotational direction of the spindle shaft) of the blocking tool fixing the lens, and shifting the grinder or lens in the Z-axis direction (parallel to the spindle shaft). The lens grinder 241 is a numerically controlled grinder at least triaxially controllable, and performs lens edging or beveling based on a transmitted beveling design data.

[S23] A bevel shape including a bevel position of the beveled lens is measured.

[S24] The bevel quality is inspected by comparing the bevel size and shape including the bevel position measured in Step S23 with a drawing of the bevel position written in an instruction of processing prepared based on the result operated in the beveling design operation in Step S11. An outward appearance inspection is executed to check occurrence of scratches, burrs, chips, or the like on the lens due to edging or beveling.

[S25] The lenses which have passed the quality inspection out of lenses before edging after the above lens processing, or lenses after edging or beveling, which have produced via edging or beveling according to designation are shipped to the optician's shop 100.

It should be noted that when either the right or left eye lens is broken, an order for a single lens for the right or left eye is also received. In such a case, if the optical performance of the lens on the non-damaged side can be found, the lens design for a lens on the damaged side can be successfully carried out using the optical performance data of the non-damaged lens, enabling to supply the lens on the damaged side. Furthermore, though lens design is carried out on the assumption that the object point is at an infinite distance as a technique for lens design in this example, needless to say that it is also acceptable to perform lens design on the assumption that the object point is at some limited distance other than the infinite distance.

INDUSTRIAL APPLICABILITY

The present invention is usable when manufacturing and supplying spectacle lenses which ensure optical performance within a permissible range, have excellent outward appearance at the same time, and can perform well-balanced and comfortable binocular vision.

Explanation of Numerals and Symbols
   100 OPTICIAN'S SHOP
   101 CUSTOMER SIDE COMPUTER
   102 FRAME SHAPE MEASUREMENT EQUIPMENT
   200 PLANT
   201 MAINFRAME
   300 COMMUNICATION LINE

The invention claimed is:

1. A method of manufacturing a spectacle lens, specifically designing and manufacturing right and left spectacle lenses whereby a spectacle is constituted, having different prescriptions including dioptric power between right and left eyes, wherein when said difference of prescriptions including dioptric power is a prescribed value or more between the right and left eyes, said method comprises:

selecting curvatures of first and second refracting surfaces of at least one of the right and left spectacle lenses based on a dominant eye ratio, so that a difference in curvature of the first refracting surface between the right and left spectacle lenses is within a prescribed range, after respective right and left spectacle lenses are made to fulfill the prescription conditions including dioptric power and the optical performance of the right and left spectacle lenses are within a permissible range, assuming that refracting surfaces on the front object side of right and left spectacle lenses are taken as a first refracting surface and the rear eyeball side thereof are taken as a second refracting surface, when the curvature of the first and second refracting surfaces of right and left spectacle lenses is designed, wherein the dominant eye ratio is the ratio of the optical performance index of the spectacle lens for the dominant eye side to that of the spectacle lens for the non-dominant eye out of the right and left eyes, the optical performance index is exponentiation of the distinct vision field spatial extent in the optical performance of respective spectacle lenses for the right and left eyes, expressed by index of I, (Di, Bi) wherein the power of the first refracting surface is Bi, measured in dopters, and the dioptric power of the prescription is Di, measured in diopters, therefore the optical performance index of the spectacle lens for the dominant eye is expressed by I (Dmj, B1) where the power of the first refracting surface of the lens for the dominant eye is B1 and the dioptric power of the prescription is Dmj, while the optical performance index of the spectacle lens for the non-dominant eye is expressed by I (Dmn, B2) where the power of the first refracting surface of the lens for the non-dominant eye is B2 and the dioptric power of the prescription is Dmn, and therefore, the aforementioned dominant eye ratio is expressed by I (Dmj, B1):I (Dmn, B2) which is the ratio of the optical performance indexes of the left and right spectacle lenses.

2. The method of manufacturing a spectacle lens according to claim 1, wherein the difference in dioptric power between the right and left eyes is 0.5 dioptric power unit of refracting power of a spectacle lens, referred to as D, hereinafter, or more when dioptric power in the prescriptions contains plus dioptric powers, while the difference in dioptric power between the right and left eyes is 1.0 D or more when the prescription of the aforementioned dioptric power contains minus dioptric powers, and at the same time, a difference in curvature between the first refracting surfaces of the right and left spectacle lenses is 1.0 D or less.

3. The method of manufacturing a spectacle lens according to claim 1,
wherein said optical performance is at least one out of astigmatism, curvature of field, and distortion aberration.

4. The method of manufacturing a spectacle lens according to claim 1,
wherein selection of the curvature of the first refracting surface of at least one of the right or left spectacle lens is used when making the curved surface, specifically an aspheric surface.

5. The method of manufacturing a spectacle lens according to claim 1,
wherein said dominant ratio is defined in a range from 4:6 to 3:7 so as to give precedence to the optical performance index of the spectacle lens for the non-dominant eye over that of the spectacle lens for the dominant eye but the precedence is not protruded when dynamic recognition of depth in space is required, while on the contrary, the dominant eye ratio is defined in a range from 6:4 to 7:3 so as to give precedence to the optical performance index of the spectacle lens for the dominant eye over that of the spectacle lens for the non-dominant eye but the precedence is not protruded when static discrimination of an object in space is required.

6. The method of manufacturing a spectacle lens according to claim 5,
wherein whether the dynamic recognition of depth in space is required or the static discrimination of an object in space is required is determined according to dominant eye information of individual spectacle lenses wearers,
wherein the dominant eye information refers to the information of an individual spectacle lenses wearer and is a combination of a usage condition of the spectacle lenses whether a depth in space should be dynamically recognized when wearing the spectacle lenses outdoors, or whether an object in space should be statically discriminated when wearing the spectacle lenses indoors;
a functional condition of the spectacle lenses whether the depth in space should be dynamically recognized in a range from a distance vision to a near vision as is the case of driving a car, or whether an object in space should be statically discriminated mainly only in the near vision; and
a physical condition of a spectacle wearer which one of the right and left eyes is selected to be a dominant eye when gazing at an object by using the distance vision, intermediate vision, and near vision, respectively.

7. The method of manufacturing a spectacle lens according to claim 1, wherein at least one of the right and left spectacle lenses has a toric or atoric surface.

* * * * *